(12) United States Patent
Holdcroft et al.

(10) Patent No.: US 10,877,010 B2
(45) Date of Patent: Dec. 29, 2020

(54) CLYDESDALE GAS DETECTOR WITH IMPROVED SCREEN ORIENTATION BASED ON INPUT FROM ATTACHMENT SENSOR

(71) Applicant: Honeywell International Inc., Morris Plains, NJ (US)

(72) Inventors: Raymond Peter Holdcroft, Berkhamsted (GB); Nicholas Antram, Cholsey (GB); Brett Vandenbussche, Minneapolis, MN (US); Joseph Vargas, Minneapolis, MN (US); Craig Kean, Basingstoke (GB); May Wilson, Wokingham (GB); Bob Fawley, Lincolnshire, IL (US); Carl Yates, Bracknell (GB)

(73) Assignee: Honeywell International Inc., Charlotte, NC (US)

( * ) Notice: Subject to any disclaimer, the term of this patent is extended or adjusted under 35 U.S.C. 154(b) by 76 days.

(21) Appl. No.: 16/089,975

(22) PCT Filed: Mar. 30, 2017

(86) PCT No.: PCT/US2017/025068
§ 371 (c)(1),
(2) Date: Sep. 28, 2018

(87) PCT Pub. No.: WO2017/173106
PCT Pub. Date: Oct. 5, 2017

(65) Prior Publication Data
US 2019/0086378 A1 Mar. 21, 2019

Related U.S. Application Data

(60) Provisional application No. 62/426,972, filed on Nov. 28, 2016, provisional application No. 62/315,983, filed on Mar. 31, 2016.

(51) Int. Cl.
*G01N 33/00* (2006.01)
*G06F 1/16* (2006.01)
*G09G 5/38* (2006.01)

(52) U.S. Cl.
CPC ..... *G01N 33/0062* (2013.01); *G01N 33/0009* (2013.01); *G01N 33/0073* (2013.01);
(Continued)

(58) Field of Classification Search
CPC .......... G01N 33/0062; G01N 33/0009; G01N 33/0073; G01N 33/004; G01N 33/0044;
(Continued)

(56) References Cited

U.S. PATENT DOCUMENTS

| 2004/0145485 | A1* | 7/2004 | Tice | G08B 21/16 340/632 |
| 2007/0209937 | A1* | 9/2007 | Hoagland | G01N 27/122 204/424 |
| 2011/0161885 | A1* | 6/2011 | Gonia | G08B 17/10 715/847 |

(Continued)

FOREIGN PATENT DOCUMENTS

| CN | 105372395 A | 3/2016 |
| EP | 1197753 A2 | 4/2002 |

(Continued)

OTHER PUBLICATIONS

International Application No. PCT/US2017/025068, International Search Report, dated Jul. 17, 2017, 4 pages.
(Continued)

*Primary Examiner* — Harshad R Patel
*Assistant Examiner* — Nigel H Plumb
(74) *Attorney, Agent, or Firm* — Alston & Bird LLP

(57) ABSTRACT

The present invention relates generally to systems and methods for controlling the display of a gas detector. A gas detector may comprise at least one gas sensor configured to detect at least one gas in the ambient environment; a display configured to display information received from the at least
(Continued)

one gas sensor; an attachment configured to attach the gas detector to a user; an attachment sensor configured to detect when the gas detector has been attached to a user; and a processor configured to receive information from the attachment sensor, and configured to automatically control the orientation of at least a portion of the display based on the information received from the attachment sensor which indicates that the gas detector is worn by the user so as to improve the visibility of the display to the user.

19 Claims, 18 Drawing Sheets

(52) U.S. Cl.
CPC .............. *G06F 1/163* (2013.01); *G06F 1/165* (2013.01); *G06F 1/1681* (2013.01); *G09G 5/38* (2013.01); *G01N 33/004* (2013.01); *G01N 33/0044* (2013.01); *G06F 1/1698* (2013.01); *G09G 2340/0492* (2013.01); *G09G 2354/00* (2013.01)

(58) Field of Classification Search
CPC ...... G06F 1/1698; G06F 1/163; G06F 1/1681; G06F 3/013; G06F 3/04845; G06F 3/017; G06F 19/3418; G09G 5/38; G09G 5/32; G09G 2340/0492; G06T 3/60; G08B 25/016; G08B 21/12; G08B 21/14; G08B 21/182; G08B 25/10; H04W 76/10
See application file for complete search history.

(56) References Cited

U.S. PATENT DOCUMENTS

| | | | |
|---|---|---|---|
| 2013/0053661 A1* | 2/2013 | Alberth | A61B 5/1455 600/322 |
| 2014/0372940 A1* | 12/2014 | Cauwels | A61B 5/024 715/799 |
| 2015/0177207 A1* | 6/2015 | Kennard | G01N 33/007 73/31.05 |
| 2015/0212057 A1* | 7/2015 | Darveau | G01N 33/004 73/31.03 |
| 2016/0077592 A1* | 3/2016 | Bhesania | G06F 3/011 345/650 |
| 2016/0349790 A1* | 12/2016 | Connor | G06F 1/1694 |
| 2017/0011210 A1* | 1/2017 | Cheong | G06F 3/017 |

FOREIGN PATENT DOCUMENTS

| | | |
|---|---|---|
| EP | 2515108 A1 | 10/2012 |
| EP | 2887062 A2 | 6/2015 |
| JP | 2006245295 | 9/2006 |
| WO | 2006043028 A1 | 4/2006 |
| WO | 2017173106 A1 | 10/2017 |

OTHER PUBLICATIONS

International Application No. PCT/US2017/025068, Written Opinion of the International Searching Authority, dated Jul. 17, 2017, 6 pages.
International Application No. PCT/US2017/025068, International Preliminary Report on Patentability, dated Oct. 2, 2018, 7 pages.
Europe Patent Application No. 17716746.7, Communication pursuant to Rule 161(1) and 162 EPC, dated Nov. 3, 2018, 3 pages.

* cited by examiner

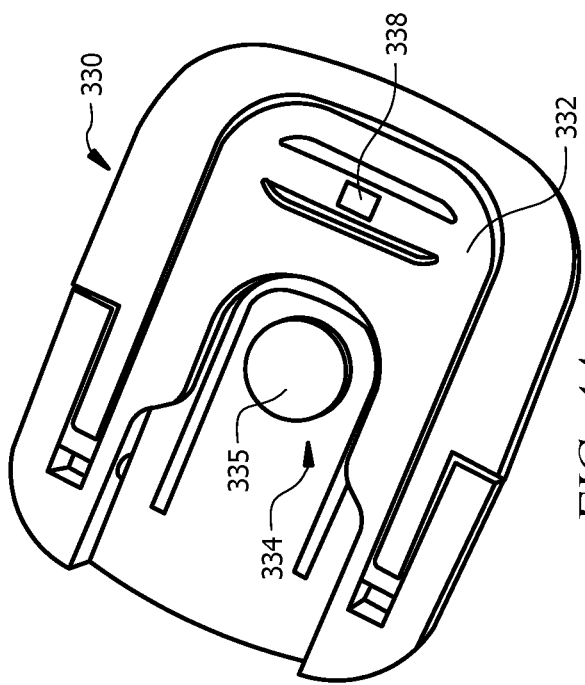
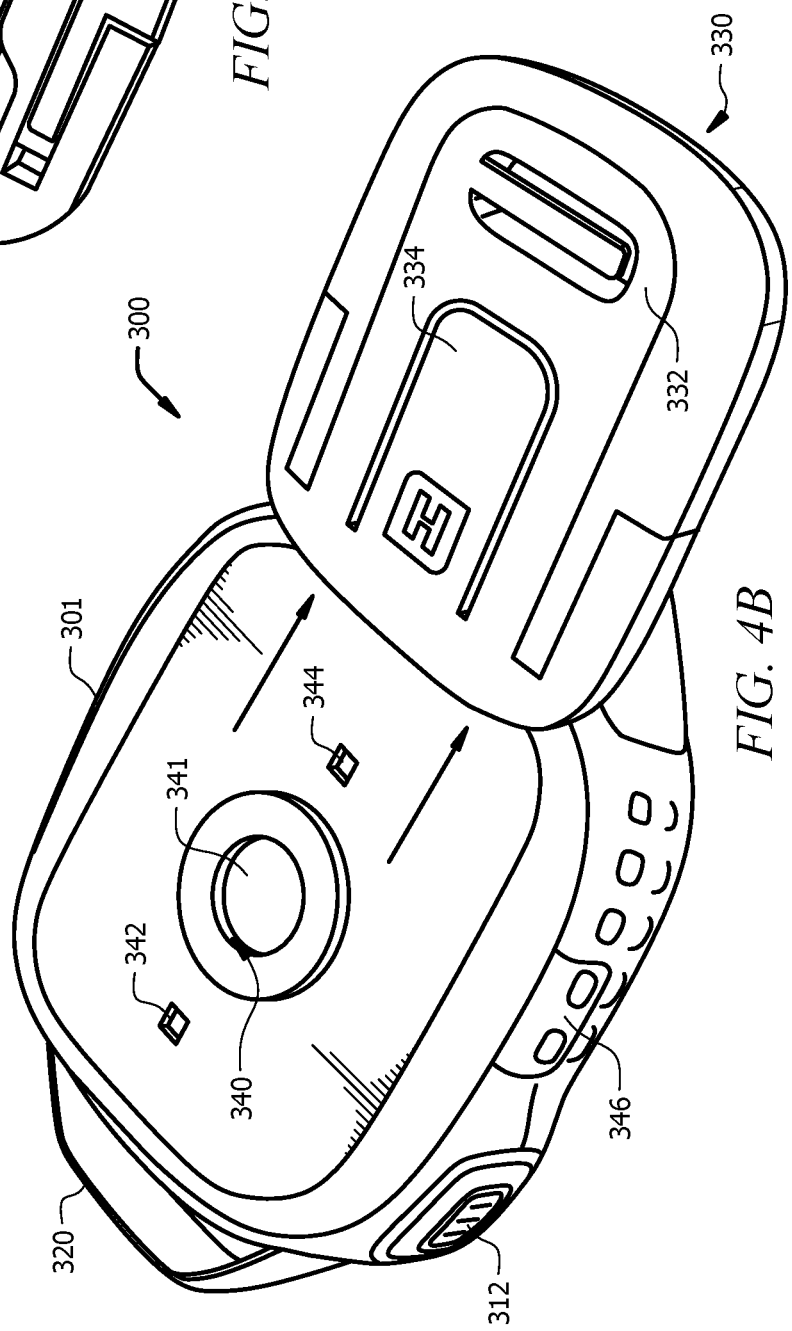
FIG. 4A
FIG. 4B

CLYDESDALE GAS DETECTOR WITH IMPROVED SCREEN ORIENTATION BASED ON INPUT FROM ATTACHMENT SENSOR

CROSS-REFERENCE TO RELATED APPLICATIONS

The present application is the National Stage International Application No. PCT/US2017/025068 entitled "Clydesdale Gas Detector" filed Mar. 30, 2017, and which claims priority to U.S. Provisional Patent Application No. 62/315,983 filed Mar. 31, 2016, and entitled "Clydesdale Gas Detector," and to U.S. Provisional Patent Application No. 62/426,972 filed Nov. 28, 2016, and entitled "Clydesdale Gas Detector," all of which are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In certain work areas and facilities, workers may carry Personal Protective Equipment (PPE) devices, such as gas detectors, with them while they are working. These gas detectors may be configured to gather data on the environment and location of the worker. PPE devices may be capable of communicating with a wireless network to communicate data to and from other wireless devices. Gas detector devices are typically used in environments containing, of having the potential to contain, harmful gases. In a safety related wireless gas detection environment, tracking a worker in a facility is important. Some facilities using wireless gas detection may comprise multiple different areas where different gasses, or different levels of gasses, may be present, wherein workers may be required to move between the different areas during their daily activities.

SUMMARY

In an embodiment, a gas detector may comprise at least one gas sensor configured to detect at least one gas in the ambient environment; a display configured to display information received from the at least one gas sensor; an attachment configured to attach the gas detector to a user; an attachment sensor configured to detect when the gas detector has been attached to a user; and a processor configured to receive information from the attachment sensor, and configured to automatically control the orientation of the display based on information received from the attachment sensor.

In an embodiment, a method for controlling the orientation of the display of a gas detector may comprise indicating that the gas detector is being worn by a user; automatically changing the orientation of the display when the gas detector is worn by a user; indicating that the gas detector is not being worn by a user; and automatically changing the orientation of the display when the gas detector is not worn by a user.

In an embodiment, a gas detector may comprise at least one gas sensor configured to detect at least one gas in the ambient environment; a display configured to display information received from the at least one gas sensor; and a hinge or pivot attached to the display, wherein the display can be rotated about the hinge or pivot, and wherein the display is operable to automatically switch orientation when rotated about the hinge or pivot, such that the display is oriented toward a user looking at the display.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIGS. 4A-4B illustrate an attachment clip for use with a gas detector according to an embodiment of the disclosure.

FIGS. 11A-11D illustrate a gas detector according to an embodiment of the disclosure.

DETAILED DESCRIPTION

Figure 1:
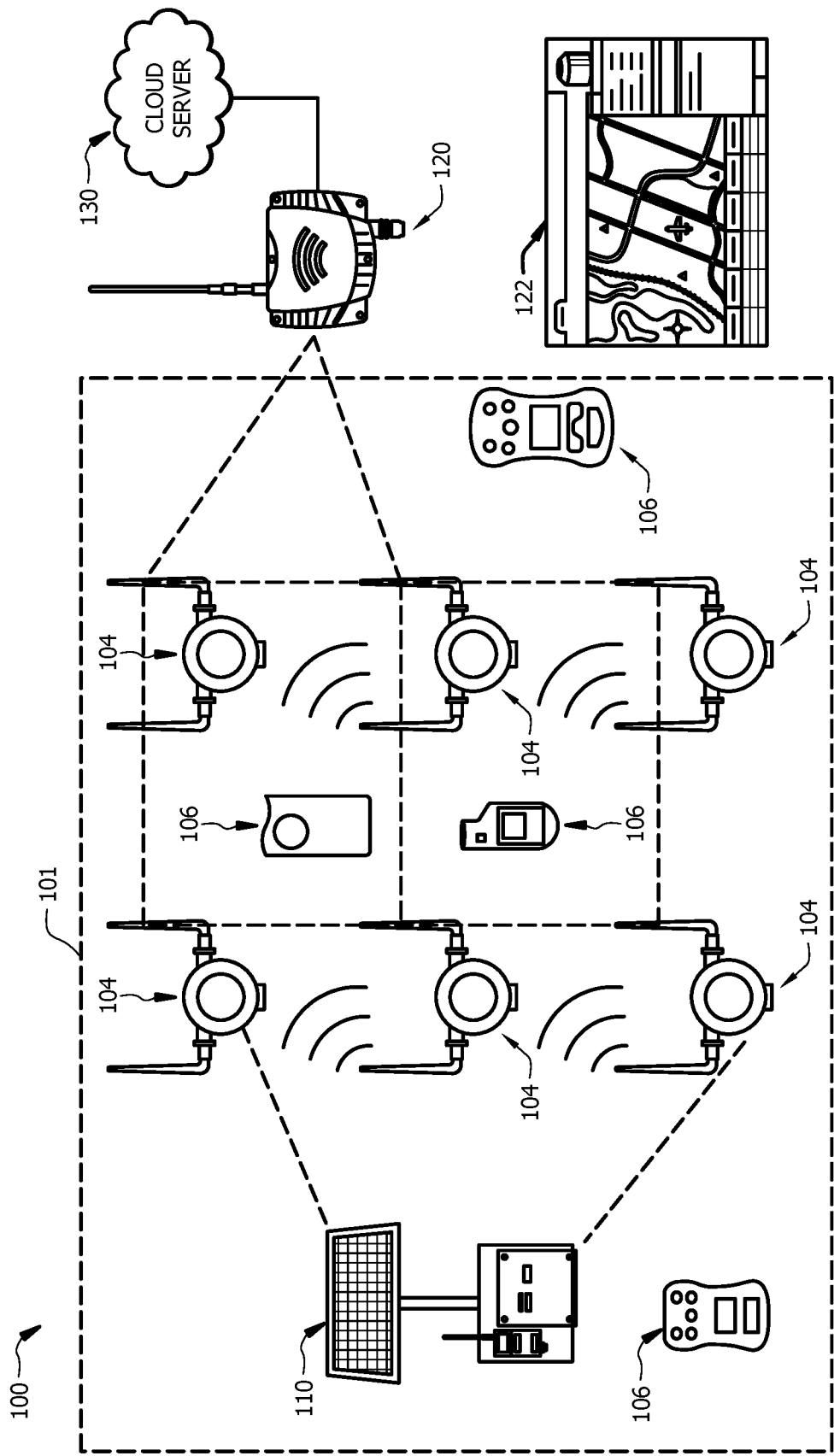
FIG. 1 illustrates a wireless communication system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Gas detectors may comprise a display for communicating sensed information to a user. The display may comprise a plurality of features for clean communication. A light-emitting diode (LED) display for a gas detector may provide clear, simplified information to the user at a quick glance. The main LED indicators use 3 colors to show status: green to represent "safe to proceed", red to represent "danger, evacuate" and orange to represent maintenance activity. Additional icons may be used when required in addition to the main LED bars to indicate action required for low battery, maintenance (bump test), calibration, data sync and sensor/filter. Pulsing LED's provide extra visibility for alerts and warnings to both users and co-workers. Sound, vibration, or other modality can be used in tandem with the visual indication to provide information to the user.

An icon display (produced by using backlit multi-color LED's or other display technologies) for a gas detector may use simple icons to display alerts and re-enforce confidence that the product is working correctly. In the field, a clear green and red display is used to provide confidence and warnings. After the job, prioritized tasks are highlighted and the system takes the user through the steps required to ready the unit for the next shift. The icons could be arranged in a single line or matrix format. The display could be a screen only interface or a touch screen device. Icons illustrated represent battery level, maintenance (bump test), calibration, Bluetooth or wireless connectivity and sensor/filter. Additional icons could be created based on required functionality and needed information. A monochrome liquid crystal display (LCD) or black and white digital display for a gas detector may use minimum messaging to provide clear information to the user in order to proceed confidently, be warned of gas detection or reminded of maintenance and data logging duties. The display could show fixed information or scroll for additional messaging. A single line color digital display for a gas detector may use minimum messaging to provide clear information to the user in order to proceed confidently, be warned of gas detection or reminded of maintenance and data logging duties. The display could show fixed information or scroll for additional messaging. The background color for the display also reinforces the messaging and indicates the status, green for 'ready' and 'safe', red for 'gas detected' and orange for syncing and maintenance requirements. The color provides additional awareness for warnings to both users and co-workers. Using a background color allows the user to more quickly understand high level information (danger or safety) without having to read the text.

A color digital display for a gas detector may present clear prioritized information in a list, using text message to remove ambiguity for the user. Icons and color indicate the status of the listed item. Information listed includes maintenance activities such as the bump test, calibration, battery level, filter, sensor and Bluetooth or wireless connectivity. A color digital display for a gas detector may use minimum messaging to provide clear information to the user in order to proceed confidently, be warned of gas detection or reminded of maintenance and data logging duties. The display could show fixed information or scroll for additional messaging. The background color for the display also reinforces the messaging and indicates the status, green for 'ready' and 'safe', red for 'gas detected' and orange for syncing and maintenance requirements. The color provides additional awareness for warnings to both users and co-workers. Using a background color allows the user to more quickly understand high level information (danger or safety) without having to read the text. A color touchscreen interface for a gas detector may use a series of icons to illustrate the products eco-system. The status of each function is communicated through the color of the icon, green representing positive, red requiring urgent attention and orange representing maintenance or data logging. After the job and maintenance colors are used to flag to the user areas that require their attention with red being the function that should be attended to first. Once addressed, the next most urgent function is highlighted, until all required actions are completed.

Referring now to FIG. 1, a communication system 100 is shown. The communication system 100 may comprise a gateway device 120 operable to receive information from a plurality of devices. The gateway device 120 may also be in communication with a cloud server 130. The gateway device 120 may also be in communication with a user interface 122, such as a computer, tablet, or other display. In some embodiments, the communication system 100 may comprise a plurality of access points 104 (which may also be known as routers, though other devices can also be used), which may be located throughout a facility 101 where gas detection (or other sensor detection) may be necessary. In some embodiments, the access points 104 may be in fixed locations within the facility 101. In some embodiments, the access points 104 may communicate wirelessly with other devices within the facility 101, and the access points 104 may communicate with other access points though the wireless mesh network within the facility 101. In some embodiments, the access points 104 may communicate over a wired connection with other devices within the facility 101. In some embodiments, each of the access points 104 may comprise a modem.

In some embodiments, the communication system 100 may comprise one or more detector devices 106 located within the facility 101. The detector devices 106 may comprise gas detector devices operable to detect concentrations of one or more gases in the air. These detector devices 106 may be mobile and carried with a worker in the facility. In some embodiments, the gas detector devices 106 may be operable to trigger alarms when the detected gas concentration moves outside of a predetermined threshold or thresholds.

In some embodiments, the gateway device 120 may receive the data from the detector device 106 and may analyze and/or process the data. For example, the gateway device 120 may use the location information to perform a triangulation algorithm to determine the actual location(s) of the detector device 106 within the facility 101. In this embodiment, the data may not be processed or analyzed locally by the detector device 106, but may instead be communicated to the gateway device 120 for analysis. In some embodiments, each of the detector devices 106 may comprise a modem. The communication system 100 may also comprise a mesh router 110 configured to provide wireless communication support for the communication system 100.

Referring to FIG. 1, the communication system 100 may be operable to wirelessly set up and activate single and multiple gas detectors 106. The communication system 100 may be configured to install settings using Bluetooth and/or other wireless communication technologies from a desktop computer or mobile device. Multiple detectors 106 can be wirelessly linked together to produce a single network for simplified communication and updating, downloading data. In the field, additional (new) detectors that enter a workspace can be set up wirelessly by receiving data from configured detectors 106 already in use in the workspace. Data logs can also be exchanged wirelessly between detectors 106, so that, in the event of a failure (battery loss, breakage) for one or more of the detectors, the information from that detector may be retained. The communication system 100 may allow for simultaneous updating of a group of gas detectors 106, wherein the updating may comprise changing of settings. The settings that are changed may include alert thresholds based on sensor reading, and the specific information that is recorded or captured by the gas detector 106. In some cases, if a situation changes for a group of workers, this may facilitate a settings change for that group of detectors 106, which may be simultaneously implemented over the wireless communication system.

Multiple detectors 106 may wirelessly link together to form a network, using Bluetooth or another wireless technology. If a detector senses gas, a warning may be communicated wirelessly to all detectors 106 in the network or/and a centralized control station having a user interface 122, so that co-workers who may not be able to see or hear a warning are informed that a worker in their network or locality has detected gas. They are also informed of the detector number or co-workers name. A Bluetooth or other wireless technology signal may be emitted from the detector 106 to a wireless communication device (such as a GPS or smart phone). On receiving the signal, the location information is pushed to a control center, which allows a Safety Manager to have real-time location of all his workers and in particular, the location of a gas detector.

Single and multiple gas detectors 106 are able to transfer and receive data from the cloud 130, either directly using Wi-Fi, or indirectly using Bluetooth and USB via a desktop or mobile computer. The wireless communication would allow for both the push and pull of data from the cloud 130 or a desktop/mobile computer via an app. Information pulled to the detector 106 would include firmware upgrades, detector deployment, settings, set point configuration, permission rights and maintenance reminders. Information pushed from the device would include data logging, permission rights and hardware status such as battery life.

In some embodiments, for worker location monitoring and determining the position of detected gas through alarm activation, single and multi-gas detectors 106 could be wirelessly tethered via Bluetooth to a smart device with global positioning system (GPS) capability. The transmitted GPS signal could show the location of the worker and detected gas if the device is alarming, to a Safety Manager using a desktop/mobile device app.

Figure 2:
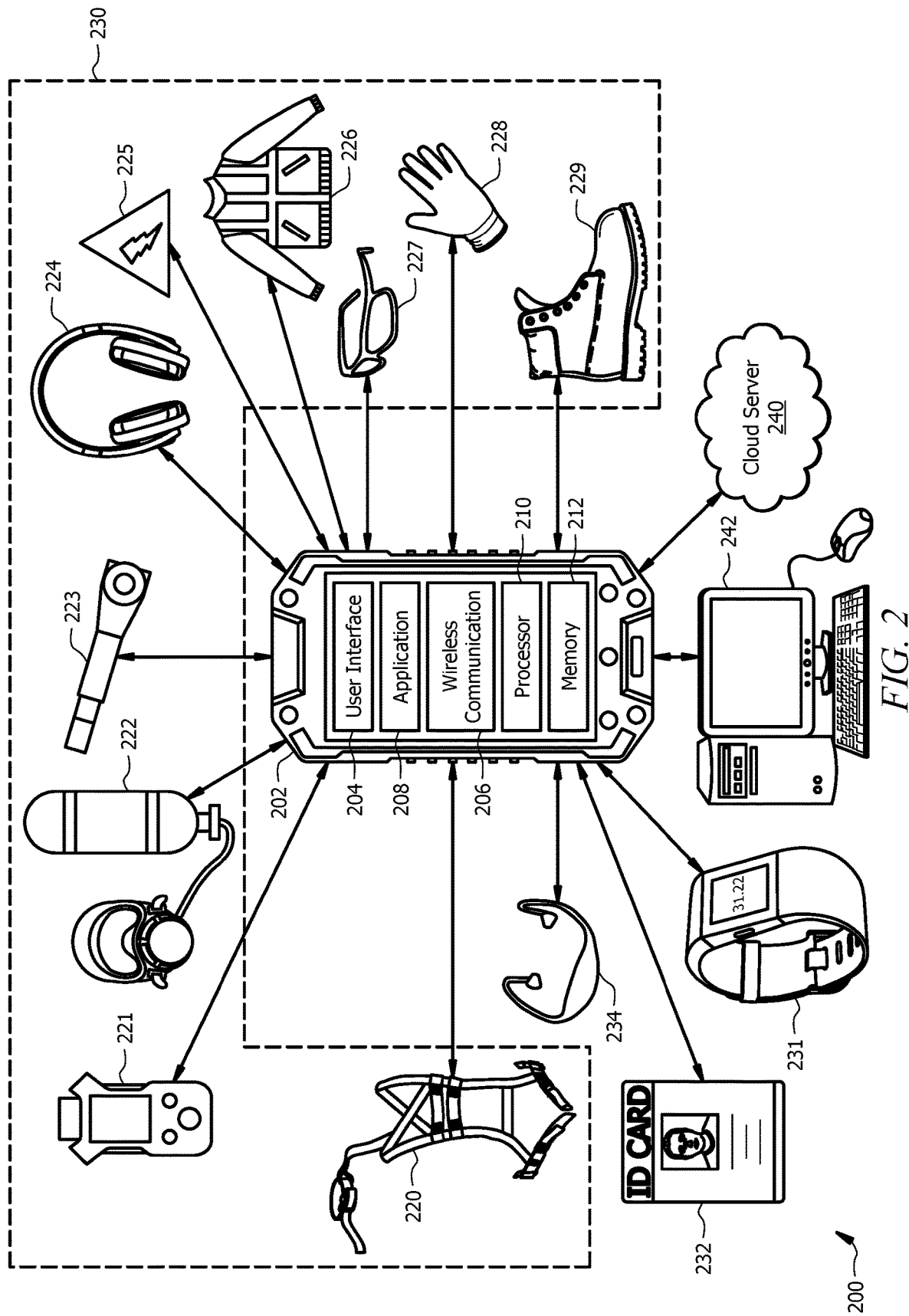
FIG. 2 illustrates a wireless communication system according to an embodiment of the disclosure.

Referring to FIG. 2, a system 200 is illustrated, wherein the system 200 may comprise a mobile device 202 and a gas detector 221, where the gas detector 221 may be connected to several products for greater worker intelligence, monitoring and functional enhancement. The mobile device 202 may comprise a smartphone, tablet, or other handheld device. The mobile device 202 may comprise a user interface 204 operable to communication information to a user and received input from a user. The mobile device 202 may comprise wireless communication elements 206, and may be operable to wirelessly communicate with a plurality of devices. In some embodiments, the mobile device 202 may be operable to communicate via Wi-Fi, Bluetooth, near field communication (NFC), radio frequency identification (RFID), radio, cellular, or any other wireless communication system.

In some embodiments, the mobile device 202 may communicate with a plurality of PPE devices 230. These PPE devices 230 may include fall protection systems 220, gas detectors 221, respiratory protection 222, a bio harness 223, hearing protection 224, electrical safety equipment 225, first responder equipment 226, eye, face, and head protection 227, body protection 228 (such as gloves), and footwear 229. The PPE devices 230 shown in FIG. 2 are examples of devices that may be worn by the user and communicate with the mobile device 202, but other PPE devices 230 may be capable of communicating with the mobile device 202 via wireless communication, as well.

Fall protection systems 220 may communicate data to the mobile device 202, such as fall detection and alert, personal airbag, predictive fall prevention, and man down alarms or alerts. Gas detectors 221 may communicate data to the mobile device 202, such as gas level readings, gas identification, exposure data, and any alarms or alerts. Respiratory protection 222 may communicate data to the mobile device 202, such as exposure count, environmental hazards, breath analysis, drug and alcohol detection, and any alarms or alerts.

The bio harness 223 may read a wearer's vital parameters, such as heart rate, electromagnetic pulse (EMP), temperature, respiratory rate, etc. The bio harness 223 may be operable to communicate the wearer's vital parameters to the mobile device 202. Hearing protection 224 may include active hearing protection and/or passive hearing protection, ear buds, ear muffs, and other hearing protection devices. The hearing protection 224 may communicate data to the mobile device 202, such as virtual training, process verification, active noise cancelling information, in-ear dosimetry, and any alarms or alerts.

Electrical safety equipment 225 may communicate data to the mobile device 202, such as voltage detection, wireless meters, energy harvesting, and digital work permit information. First responder equipment 226 may communicate data to the mobile device 202, such as physiological monitoring and tracking, hands-free navigation, incident management, and air quality information. In some embodiments, first responder equipment may include other PPE devices, such as gas detectors, bio harnesses, location devices, etc.

Eye, face, and head protection 227 may include glasses, goggles, helmets, face shields, face masks, among other devices. Eye, face, and head protection 227 may communicate data to the mobile device 202, such as heads up display information, workflow navigation, hands-free work, voice control, and impact sensing. Gloves 228 and other body protection may include protective clothing, hoods, suits, gloves, sleeves, aprons, among other body protection. Body protection 228 may communicate data to the mobile device 202, such as vital signs monitoring, stress and comfort, replacement notification, compliance monitoring, and asset tracking. In some embodiments, the bio harness 223 may be incorporated into body protection 228. Footwear 229 may communicate data to the mobile device 202, such as slip hazards, liquid detection, fatigue monitoring, location services, and step and/or wear counts.

The mobile device 202 may receive data, as described above, from any number of PPE devices 230. The mobile device 202 may comprise an application 208 operable to receive, process, and compile the data into an easy-to-read format. The mobile device 202 may also comprise a processor 210 and a memory 212, wherein the application 208 is stored in the memory 212 and executed by the processor 210. The application 208 may display the data via the user interface 204 of the mobile device 202. In some embodiments, some of the information may be combined to simplify the display, and may be combined to generate a health status for the user.

In some embodiments, the mobile device may also communicate with other devices, such as a user identifier (ID) 232, a smart watch 231, and a Bluetooth headset 234. The user ID 232 may communicate user identification information to the mobile device 202. In some embodiments, the application 208 may be operable to associate data received from the PPE devices 230 by the mobile device 202 with the user identification information (or data). The smart watch 231 may act as a second user interface for the mobile device 202, and may display information from the application 208 of the mobile device 202, and may also receive input from the user that is communicated to the mobile device. Additionally, a user may wear a Bluetooth or wireless headset 234, wherein the application 208 of the mobile device 202 may send information to the user via the headset 234, such as an audio message or alert.

In some embodiments, the mobile device 202 may store the data received from the PPE (and other) devices. The mobile device 202 may also communicate the data to a cloud server (or storage, or network) 240, wherein the data may be accessed by other systems for monitoring purposes. In some embodiments, a plurality of mobile devices carried by a plurality of users may communicate data to the cloud server 240. Different management systems may analyze the data to generate monitoring reports for a group of users. In some embodiments, the mobile device 202 may communicate with a central monitoring station 242, wherein the mobile device 202 may send data to the central monitoring station 242. In some embodiments, the central monitoring station 242 may receive data from the mobile device 202 via the cloud server 240.

In some embodiments, the cloud server 240 may provide access to a public network for the data received by the mobile device 202, while the PPE devices 230, other devices, and central monitoring station 242 may communicate via a private or enterprise network. In some embodiments, the mobile device 202 may be operable to communication with other mobile devices. For example, in the event of an alarm, the mobile device 202 may be operable to send a message to one or more preconfigured identifier, such as a mobile number and/or email address.

In some embodiments, the mobile device 202 may handle (or facilitate) all communication between the PPE devices 230 and the cloud server 240 and central monitoring station 242. In other words, the PPE devices 230 may not directly communicate with the central monitoring station 242 and/or cloud server 240. Combining all of the communication from all of the PPE device into one communication channel between the mobile device 202 and the central monitoring station 242, or between the mobile device 202 and the cloud server 240, may serve to clear up wireless communication channels that may be used if all of the PPE devices 230 individually communicated with either the central monitoring station 242 or the cloud server 240.

In other embodiments, one or more of the PPE devices 230 may be enabled to communicate with the central monitoring station 242, for example if communication is lost between the mobile device 202 and the central monitoring station 242. This may occur if the mobile device 202 loses battery life, is damaged, or otherwise unable to communicate with the central monitoring station 242. Therefore, a PPE device may receive a notification that the mobile device 202 is not communicating with the central monitoring station 242, and may activate communication between the PPE device and central monitoring station 242.

In some embodiments, the application 208 may be a sub-system of a Personal Safety Ecosystem (PSE) on the mobile device 202. The PSE may comprise multiple application or device managers on the mobile device 202.

In some embodiments, the gas detector 221 may communicate directly with one or more of the PPE devices 230. For example, the gas detector 221 may wirelessly communicate with the bio harness 223 (which may comprise a physiological/biometric monitoring band sensing pulse rate, motion and skin temperature). The gas detector 221 may wirelessly communicate with a heads up display of the eye, face, and head protection 227. The gas detector 221 may wirelessly communicate with the hearing protection 224, such as an electronic ear muff for sound and voice control. The gas detector 221 may wirelessly communicate with a GPS enabled device for real-time location monitoring. The gas detector 221 may wirelessly communicate with the central monitoring station 242, which may comprise a desktop/mobile computer.

Figure 3A:
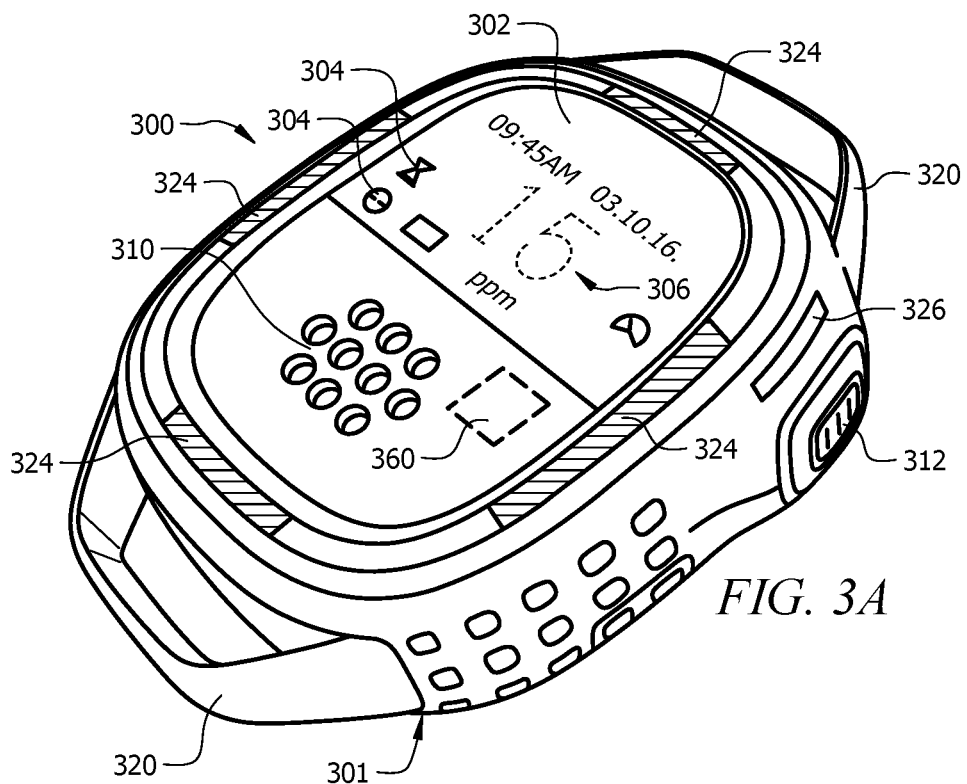
FIGS. 3A-3B illustrate a gas detector according to an embodiment of the disclosure.
Figure 3B:
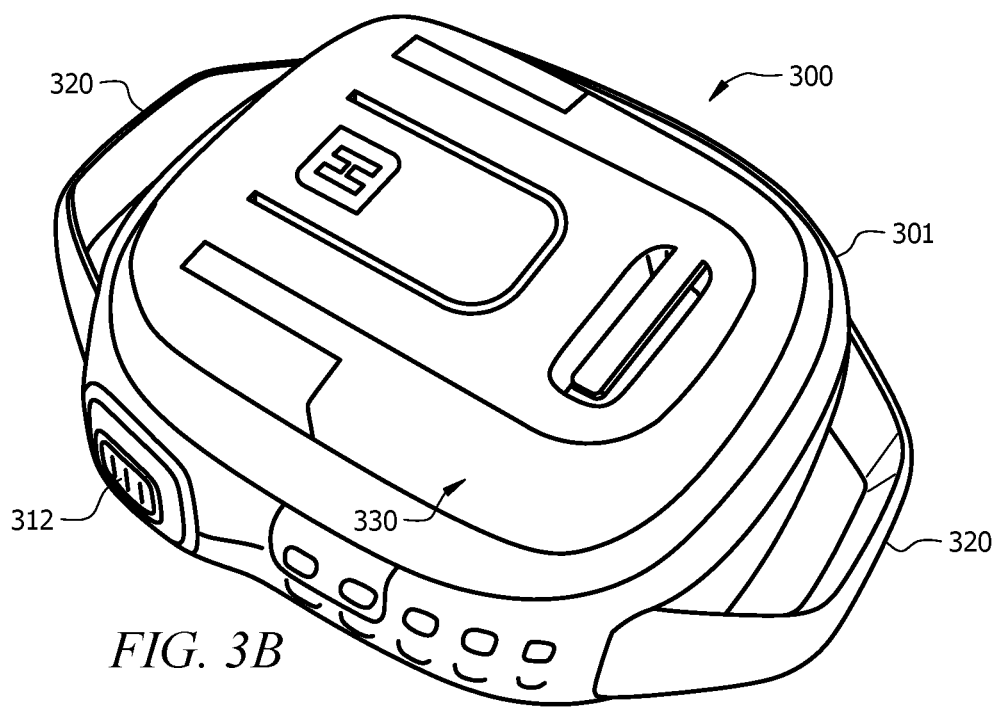

Referring to FIGS. 3A-3B, a gas detector 300 may comprise at least one gas sensor 310 configured to detect gas in the ambient environment. The display 302 of the gas detector 300 may comprise icons 304, numbers 306, readings, time, date, units, and other relevant information about the sensed gas by the sensor 310 as well as the functionality of the gas detector 300. The gas detector may comprise an internal processor 360 configured to receive and process information from the sensor 310, control the display 302, and control communications to and from the gas detector 300.

The display 302 may be configured to rotate in response to one or more actions by the user. As an example, the display 302 may rotate upon attachment of the gas detector 300 to a user via a clip 330. At least a portion of the display 302 may rotate upwards to face the user when the gas detector 300 is attached to the user, such as via clothing. When the gas detector 300 is removed, the display 302 may rotate down, so that the information is viewed the right way up from a front-facing position. This action may be triggered by the clipping and unclipping of the gas detector 300 to the user via the clip 330. For example, a sensor 341 (shown in FIG. 4B) located within an attachment clip 330 may indicate when the gas detector is worn or not worn. It may be possible to override the auto-rotation and set up the device display orientation as a fixed display to suit the user's preference.

As another example, the display 302 of the gas detector 300 may be configured to rotate when the device moved in a certain way by the user. When attached to the user in a typical manner, with the display front facing, the display may be oriented such that someone facing the user may be able to read the display. The clip 330 may allow for the gas detector 300 to be lifted up to be viewed by the user. In some embodiments, the display 302 (and/or gas detector 300) may be attached to the user (via their clothing) on a hinge or pivot, such that a portion of the gas detector 300 and/or display 302 may be easily rotated toward the user's face. When the gas detector 300 and/or display 302 are rotated, the orientation of the display 302 may automatically change so that the user may view the display 302 in the right direction.

In some embodiments, one or more reflective and luminescent elements may be incorporated into the external housings of the gas detector 300, meeting high visibility requirements without having to change the product color. In some embodiments, the gas detector 300 may comprise one or more reflective strips 324 located on the housing 301 of the gas detector 300.

In some embodiments, to provide a confirmation to the user that the gas detector 300 is on and working, the gas detector 300 may utilize the display 302 and/or an indicator light 326 to provide a confidence message that the gas detector 300 is functioning correctly. For example, a slow pulsing or flashing from the indicator light 326 may indicate that the gas detector 300 is functioning, while not requiring a significant increase in power usage. The indicator light 326 may have a soothing rhythm and frequency so as not to cause an unwanted distraction for the user.

In some embodiments, the gas detector 300 may comprise one or more buttons 312 configured to receive inputs from a user and allow the user to control certain functions of the gas detector 300. In some embodiments, a button 312 may be located on the side or edge of the gas detector 300 making it easily accessible to a user. In some embodiments, the button 312 may comprise a rotary dial used to navigate through menus on the gas detector 300. The menus may comprise additional sensor information, settings, battery life, among other things. The rotary dial button 312 may rotate to switch between menus and/or options. On pressing the rotary dial button 312, a selection may be made to activate one or more functions. The rotary dial button 312 may be located on the side of the gas detector, to be conveniently accessed by a user.

In some embodiments, the gas detector 300 may comprise one or more attachment elements 320 configured to interface with a variety of straps and/or clips to provide flexibility for how users can wear and/or carry the gas detector 300. These accessories are shown in more detail in FIGS. 5A-5F.

Referring to FIGS. 4A-4B, the attachment clip 330 for a gas detector 300 is shown in more detail. The attachment clip 330 may enable the gas detector 300 to be rotated on a ratchet, so that the user can adjust the orientation of the gas detector 300 and optionally flip the unit upside down, so that the display is positioned towards the user. In this example, the display 302 (not shown) may or may not rotate when the housing 301 of the gas detector 300 is rotated. The attachment clip 330 may be configured to lock into a position until pressure is applied by a user to move the clip 330 to a different position. The ratcheting mechanism of the clip 330 may rotate in a circular motion from one position to the next, and the ratcheting mechanism may move in one direction or in both directions. A tight locking ratchet may provide this type of mechanism.

FIGS. 4A-4B illustrate multiple views of a gas detector 300 comprising an adjustable attachment clip 330. The clip 330 may comprise a low prole, removable clip. FIG. 4A shows an attachment surface of the clip 330, and FIG. 4B shows the opposite surface of the clip 330 as the clip 330 would be attached to the housing 301 of the gas detector 300. The clip 330 may comprise a first flexible arm 332 and a second flexible arm 334. The second flexible arm 334 may comprise a disk 335 configured to fit into a hole 340 of the gas detector 300. The disk 335 may be biased into the hole 340, and therefore lock with the hole 340, by the second flexible arm 334.

In some embodiments, the clip 330 may attach the gas detector 300 to a user's clothing, strap, or other wearable element by trapping a portion of the element between the disk 335 and the hole 340. For example, a portion of fabric may slide under the second flexible arm 334 and be trapped between the hole 340 and disk 335. In some embodiments, the gas detector 300 may comprise a plunger 341 located within the hole 340, wherein a user may control the plunger 341 by pressing one or more release buttons 346, causing the plunger 341 to lift the disk 335 and allow for the clip 330 to be removed from a user's clothing, and/or allow for the clip 330 to be removed from the back of the gas detector 300 entirely. In some embodiments, the plunger 341 may also function as an attachment sensor 341, wherein movement of the plunger, compression of the plunger, or another similar input may indicate when the gas detector 300 is being worn by a user.

The first flexible arm 332 may comprise a tab 338 configured to fit into one or more recesses 342 and 344 of the gas detector 300. The tab 338 may be biased into the recess 342 and/or recess 344, and therefor lock with the recess, by the first flexible arm 332. As shown in FIGS. 4A-4B, the clip 300 may be configured to rotate about the hole 340, where the tab 338 may lock with one of the recesses 342 and 344 to lock the clip 330 in place. Once the clip 330 is fitted, it can be rotated 180 degrees by moving the tab 338 between the two recesses 342 and 344. When a user is wearing the gas detector 300, the clip 330 allows the user to rotate the gas detector so that the display is facing up towards the user's face. This way, the user may be able to see the display without removing the gas detector 300 from their clothing.

Referring to FIGS. 5A-5F, a gas detector 300 may comprise one or more attachment elements 320 and/or hole 340 (described above) configured to interface with a variety of straps and/or clips to provide flexibility for how users can wear and/or carry the gas detector 300. As shown in FIGS. 5A-5F, the gas detector 300 may comprise a variety of shapes and sizes. The gas detector 300 may be configured to connect directly to other PPE, such as hard hats, gloves, harnesses, or other accessories. Accessories include a wrist and forearm band for wearing over clothing, an upper arm band, a clip and a pendant strap.

Figure 5A:
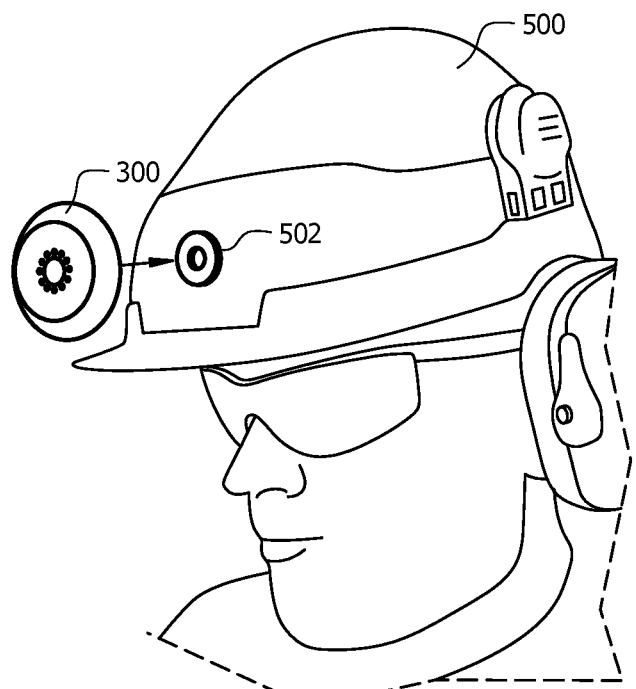
FIGS. 5A-5F illustrate a gas detector being worn by a user according to an embodiment of the disclosure.
Figure 5B:
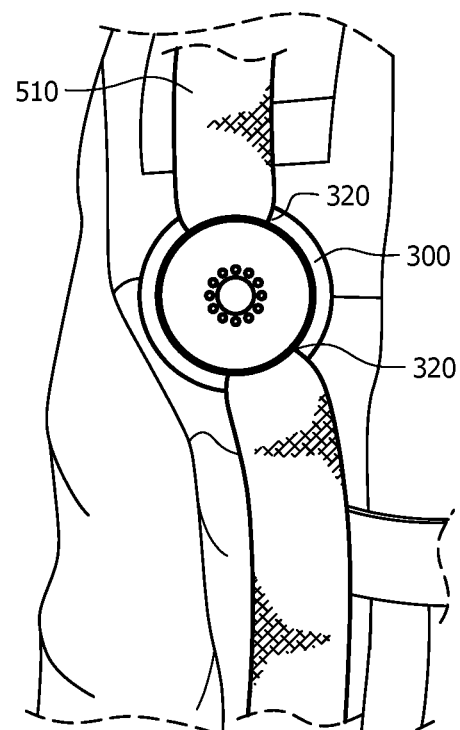
Figure 5C:
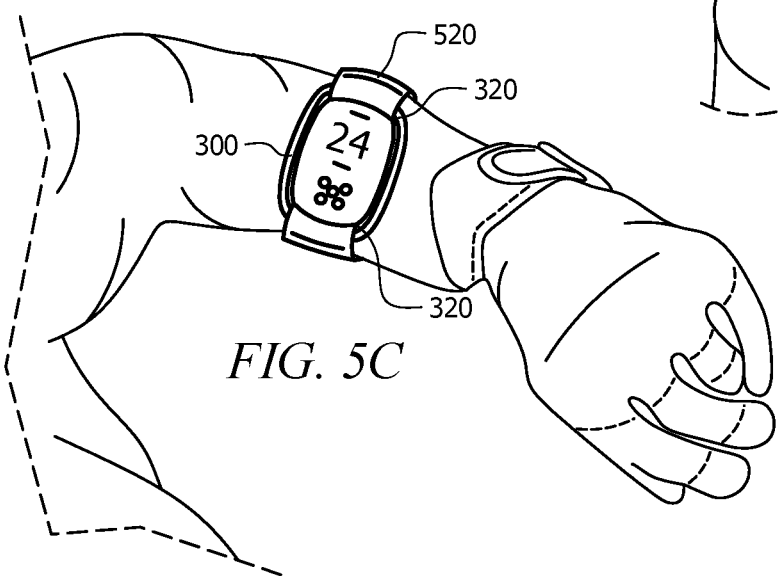
Figure 5D:
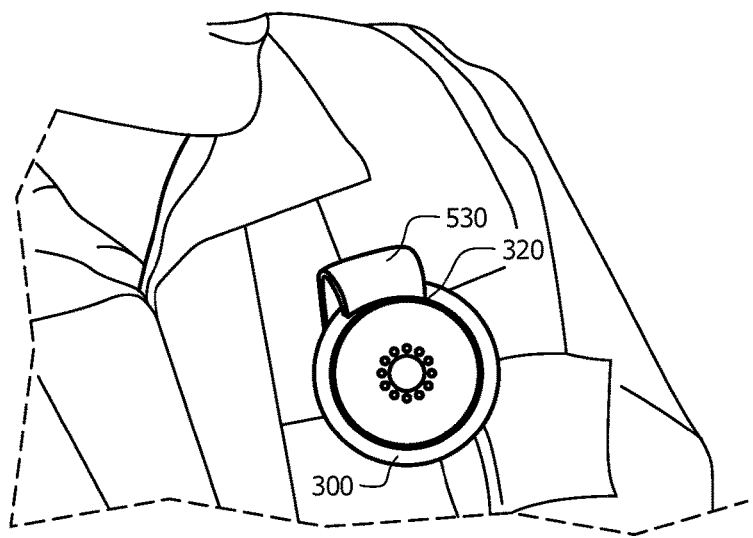
Figure 5E:
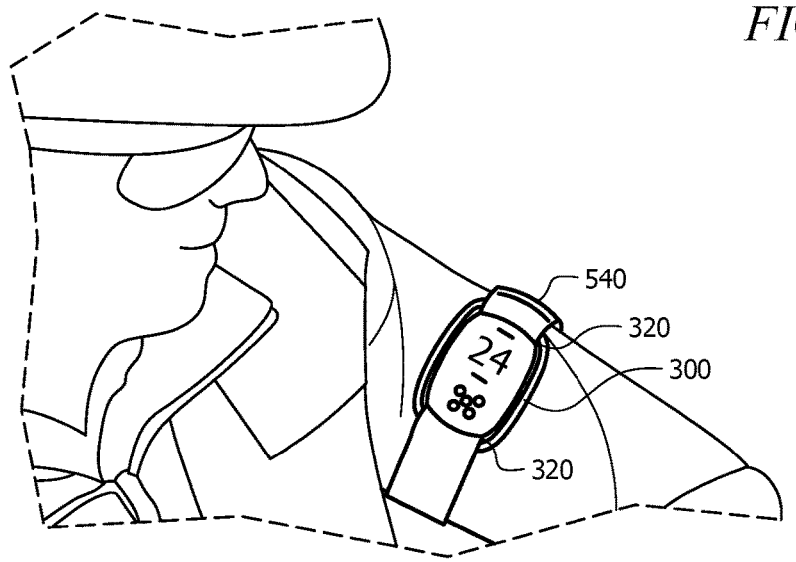
Figure 5F:
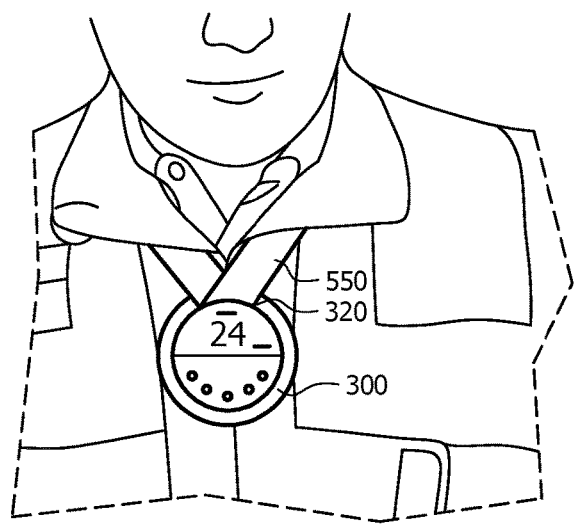

In FIG. 5A, the gas detector 300 may attach to a clip 502 on a user's helmet 500. In some embodiments, the attachment mechanism between the gas detector 300 and the helmet 500 may be similar to the attachment between the gas detector 300 as the clip 330 described in FIGS. 4A-4B. In FIG. 5B, the gas detector 300 may attach to a harness strap 510 via attachment element(s) 320. In FIG. 5C, the gas detector 300 may attach to a watch or arm strap 520 via attachment element(s) 320. In FIG. 5D, the gas detector 300 may attach to a badge or clip 530 via attachment element(s) 320. In FIG. 5E, the gas detector 300 may attach to an arm strap 540 via attachment element(s) 320. In FIG. 5F, the gas detector 300 may attach to a pendant strap 550 via attachment element(s) 320.

In some embodiments, a gas detector may be designed as a clip, rather than a device with a small alligator clip attached to its back. The clip mechanism would allow for greater opening of the clip jaws and tension control. The gas detector could be attached to a greater variety of clothing, both thicker and thinner than common work clothes as well as other PPE items, equipment and fixtures.

In some embodiments, a gas detector may comprise a soft sensor pack that can be stitched, or zipped as a pocket replacement, into work clothing such as a coverall or jacket. Additionally, the soft sensor pack could be applied temporarily but securely, using Velcro or clothing loops. The soft sensor pack may include visual, sound, and vibration alarms with status information for the user using visual indication. This gas detector could also communicate wirelessly or wired to other devices worn or carried by the user. The soft sensor pack may not inhibit the movement of the user.

In some embodiments, a gas detector may comprise a flexible LCD providing status to both the user and nearby co-workers. The flexible display could be a 'C' shaped band that attaches to the workers clothing, or the display could be integrated as part of the clothing. The display could link wirelessly or through a wired connection to a gas detector carried by the user. Alternatively, the arm wrap display could house flexible electronics making it a self-contained detector pack with a flexible LCD. The display may be larger than typical gas detector displays, and may comprise bendable or flexible LCD. In some embodiments, the gas sensors may be separate from the display, while in other embodiments, the gas sensors may be incorporated into the display. The display may wrap around a user's upper arm, or it could also be worn or located on another part of the body.

In some embodiments, a gas detector may be fitted or incorporated into a LED light band. This allows the gas detector to be worn anywhere on the arm or other bodily part where it appropriately fits. The light band may communicate status and warning alarms, allowing co-workers in noisy environments to see the warning alarms from behind, at the side, or in front of the user, providing up to 360 degrees of visual indication. In the situation of a man down incident, the LED band may provide a visual alarm status which could be activated by gas detection or a lack of motion over a set period of time. The light band may provide an extended visual alarm to other workers in the area of the alarm. The light output from the band may vary based on the situation, wherein a first color of light (such as white light) may be used for visibility and/or to indicate a non-alarm situation, a second color of light (such as green light) may be used to indicate a non-alarm situation, a third color of light (such as red light) may be used to indicate an alarm situation, and/or flashing colors may also be used to indicate other situations. In some embodiments, motion sensors and/or gas sensors may be incorporated into the band. In other embodiments, motion sensors and/or gas sensors may be in wireless commination with the band, wherein the band may comprise a wireless communication module.

In some embodiments, a gas detector may comprise additional light modules that sync wirelessly through Bluetooth with the gas detector. Common moldings used for the gas detector could also be used for the light modules. The light modules may be configured to be fixed and worn on any part of the clothing, where the visibility of the status and warning alarms are extended for both the user and co-worker to see.

In some embodiments, a gas detector may comprise a heads-up/augmented display. This display may be incorporated into a headpiece visor for in-field information, status and visual warning upon gas detection. Contextual information could also be incorporated from other worker devices, for example the amount of oxygen available in an respiratory system. Also, real time information such as evacuation instructions can be provided on the display.

In some embodiments, a gas detector may be wirelessly connected to electronic ear defenders and intelligent headphones, to provide voice information for status, maintenance requirements and gas warnings. Tone could also be used to provide audible feedback to individual workers and those in a connected network. Voice information helps to remove ambiguity, provide calm instruction and be adapted for local dialect and different languages. Contextual information could also be incorporated from other worker devices, for example the amount of oxygen available in a self-contained breathing apparatus (SCBA). Also, real time information such as evacuation instructions can be provided.

In some embodiments, a gas detector may use a color E-ink display for lower power usage. A gas detector may also use assistive technology to increase power capacity and provide battery charging through natural sources, such as kinetic and solar energy and Wi-Fi signal conversion.

Figure 6A:
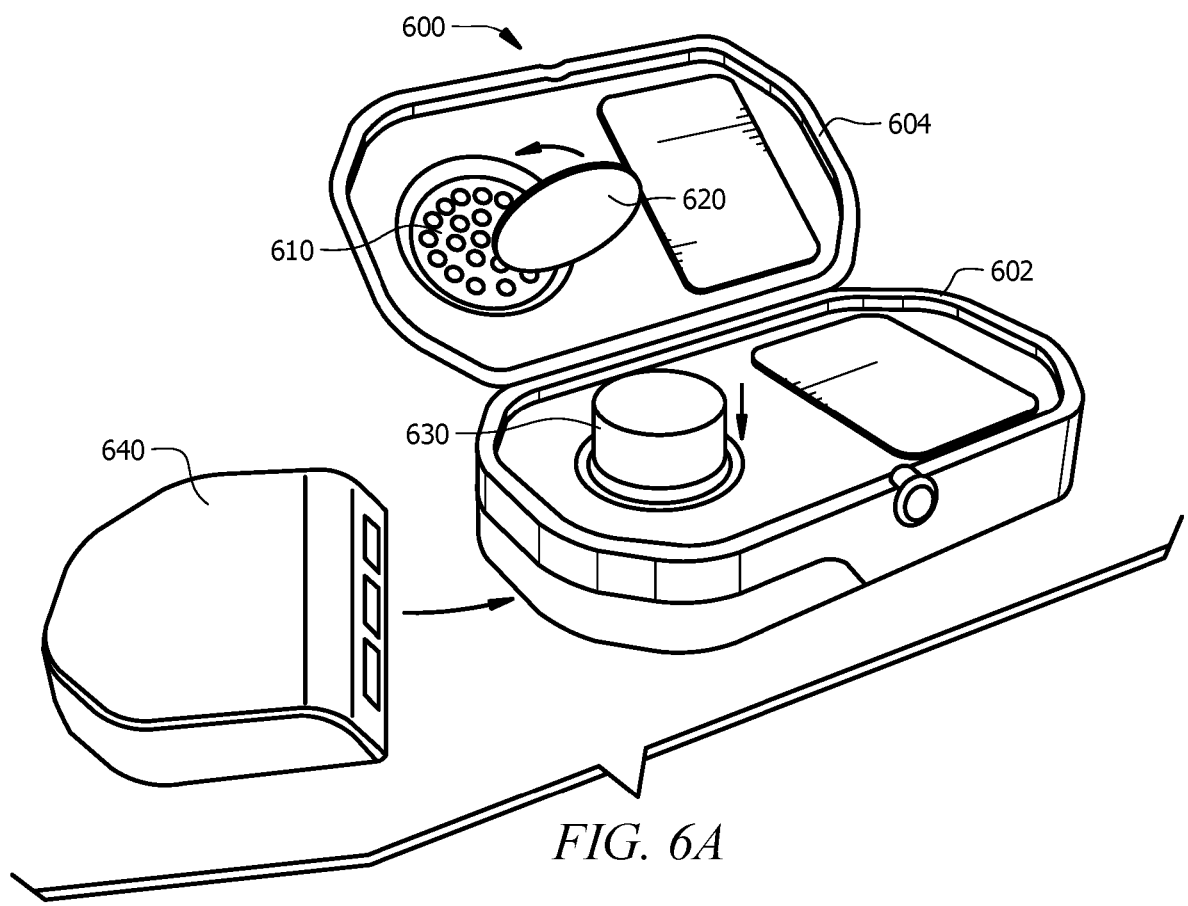
FIGS. 6A-6C illustrate a gas detector according to an embodiment of the disclosure.

Referring to FIG. 6A, a gas detector 600 may be configured to allow for quick and easy replacement of key serviceable parts, such as batteries, sensors, and/or filters. Tool-less entry through a 'push and twist' mechanism or a magnetic latch may be implemented, providing access to the battery 640, sensor 630 and/or filter 620. The housing 602 and cover 604 may be at least partially opened to access and replace the parts. In the embodiment shown in FIGS. 6A-6C, direct access to the circuitry within the gas detector 600 is not required to change the sensor 630. All accessible parts, such as the housing 602 and cover 604, the filter 620, the sensor 630, and the battery 640 may be sealed on fitting, thereby maintaining the integrity of the seal between the interior and exterior of the housing 602. The battery pack 640 could be a rechargeable battery or a casing to hold disposable batteries, providing flexibility for customers. The filter 620 and/or sensor 630 may be located near a sensor inlet 610 of the cover 604.

Figure 6B:
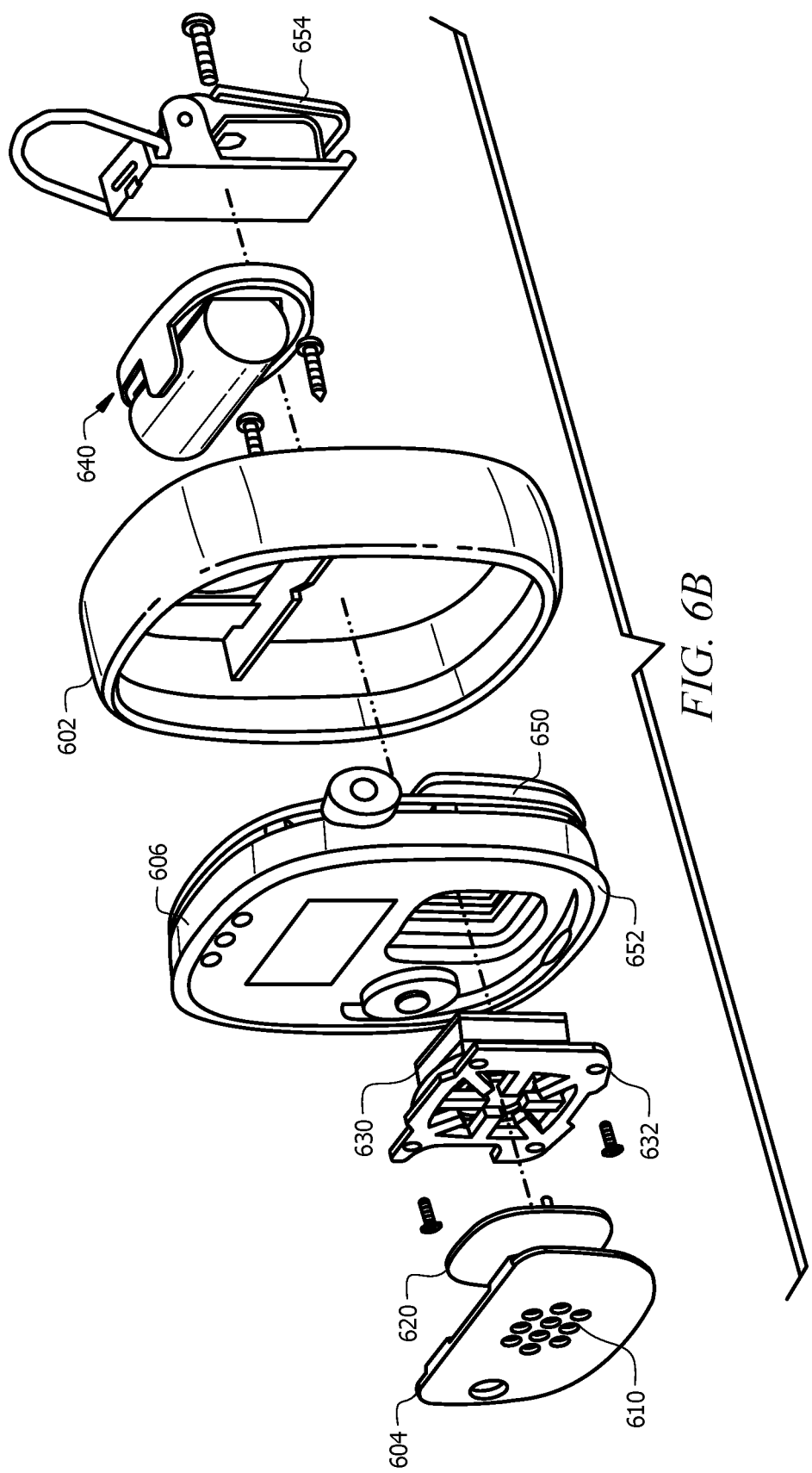
Figure 6C:
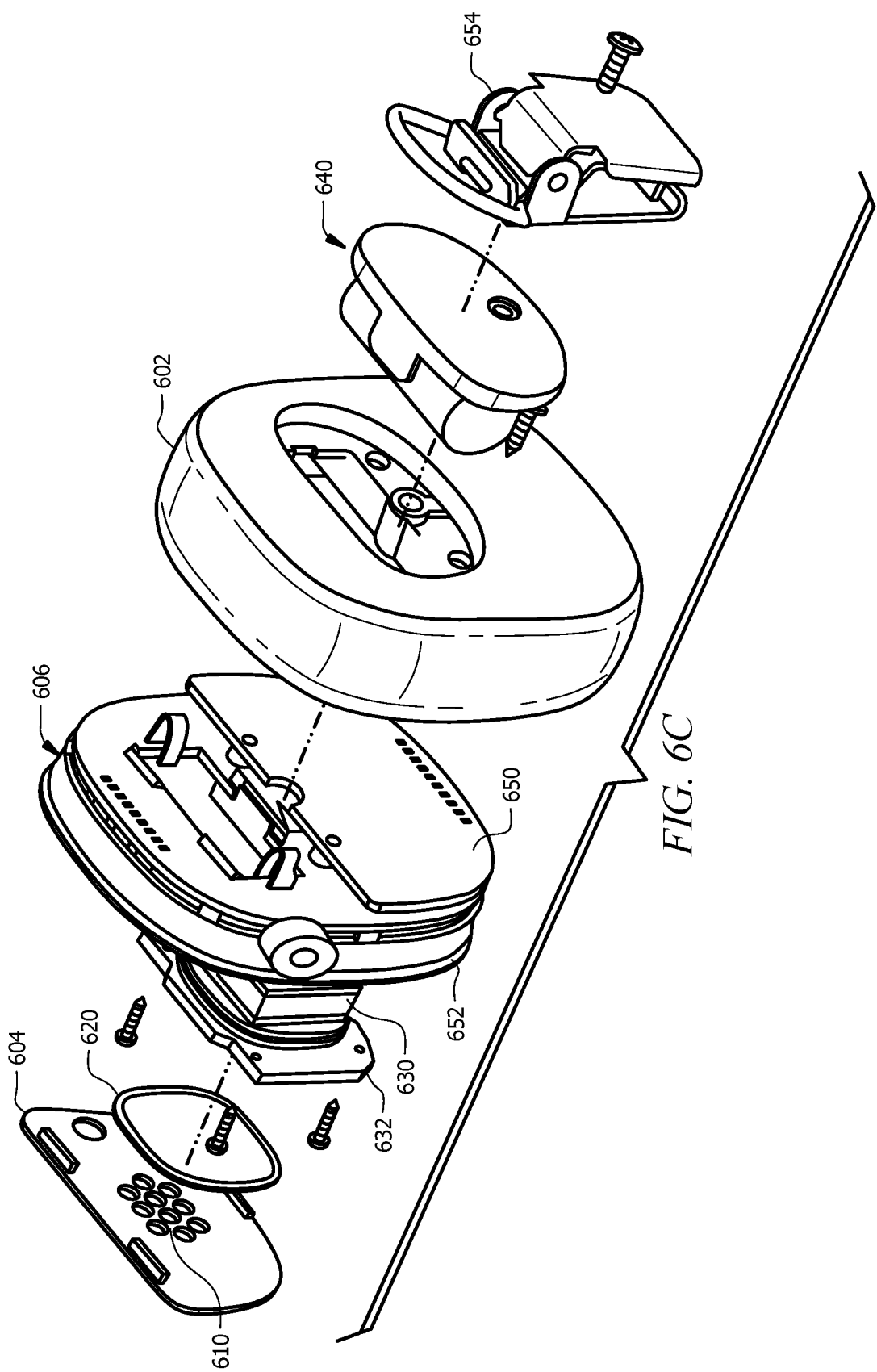

FIGS. 6B-6C illustrate another embodiment of the gas detector 600 that is configured to allow for quick and easy replacement of one or more parts of the gas detector 600. The removable front cover 604 provides access to change the filter 620 and the sensor 630 without having to open up the main housing 602 and access the circuitry, such as the printed circuit board (PCB) 650. The filter 620 may comprise colored filter papers 620 representing different gas types. The sensor 630 may sits within its own carrier molding 632 for easy removal from the PCB 650 and fast replacement, thereby protecting the PCB 650 and improving time to service the detector. The gas detector 600 may comprise a molding 652 surrounding the interior components 606 to shroud and protect the PCB 650 and components when accessing replaceable parts. The gas detector 600 may also comprise a replaceable clip 654.

Some embodiments of the disclosure may comprise methods for reducing false alarms in gas detectors, and preventing users from turning off a gas detector due to a false alarm. The gas detector may not have an on/off switch, but is turned on and off by a connection with the wearable element. This ensures the device cannot be turned off when worn for use. The gas detector may have a double action on/off button, such as 'push and twist', to prevent accidental turn off. The on/off button of the gas detector may be positioned on the underside/rear of the gas detector, making it difficult to turn off the device and providing protection from accidental deactivation. The gas detector may only be deactivated or turned off by a Safety Manager using a code-lock or wireless system. The Safety Manager may be notified wirelessly when a detector is turned off, either through text messaging, email, an app, or other wireless communication. The gas detector may not have an off state. When ready for use, the battery of the gas detector may be activated and remain on until it drains or requires recharging. The gas detector may use gesture controls for activation and sleep mode, rather than an off mode. For example, a five-second sleep activation will turn off a false alarm through a specific gesture. After five seconds the gas detector will awake to be fully functional again. A different gesture may activate a continuous sleep mode for storing the product overnight.

Figure 7A:
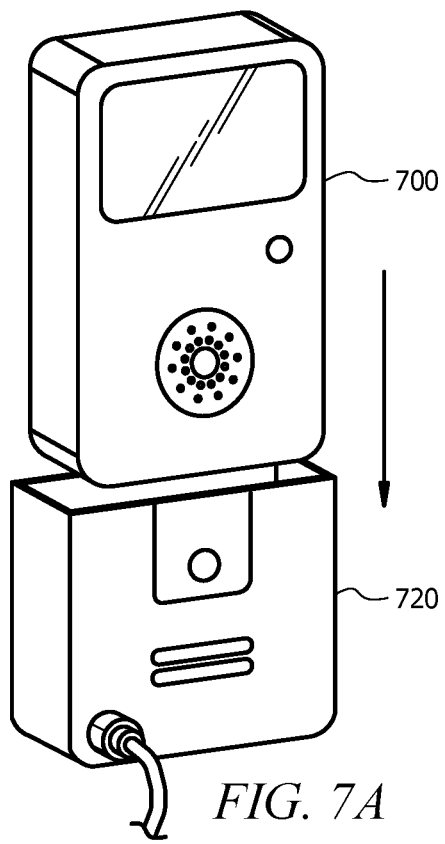
FIGS. 7A-7B illustrate a dock for use with a gas detector according to an embodiment of the disclosure.
Figure 7B:
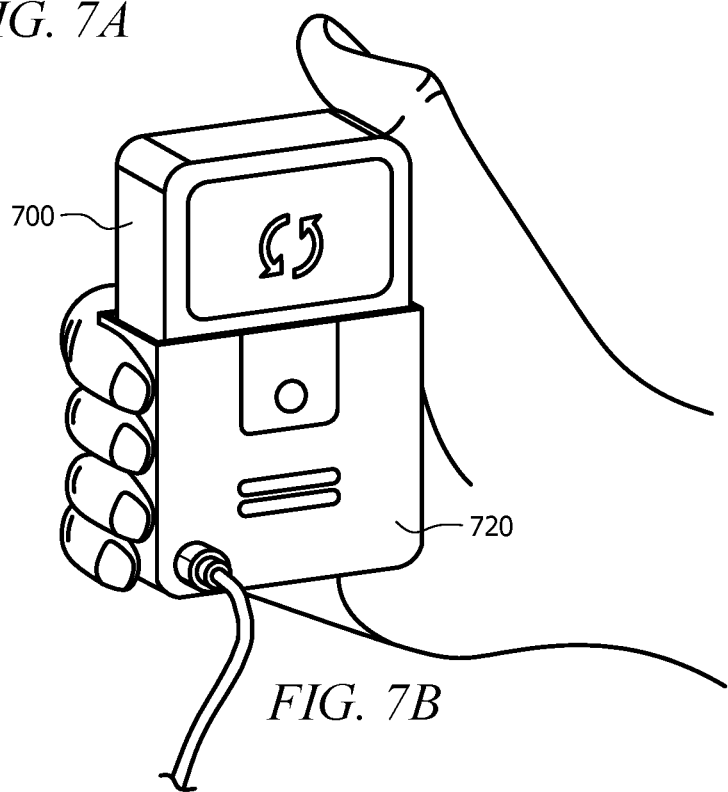
Figure 8A:
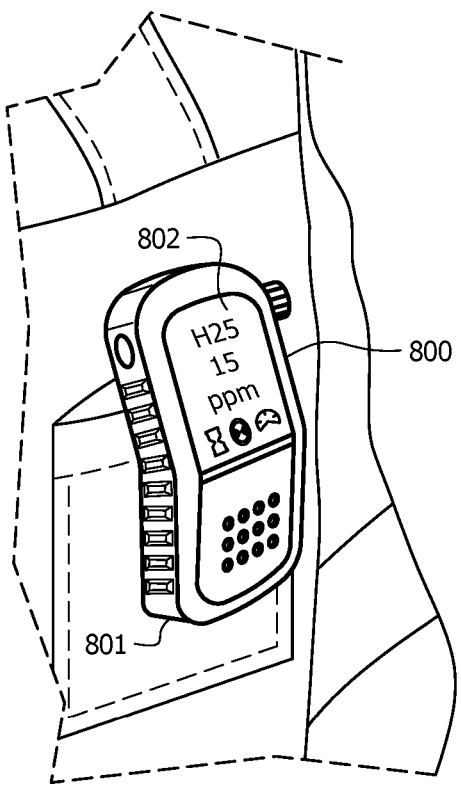
FIGS. 8A-8D illustrate a gas detector according to an embodiment of the disclosure.
Figure 8B:
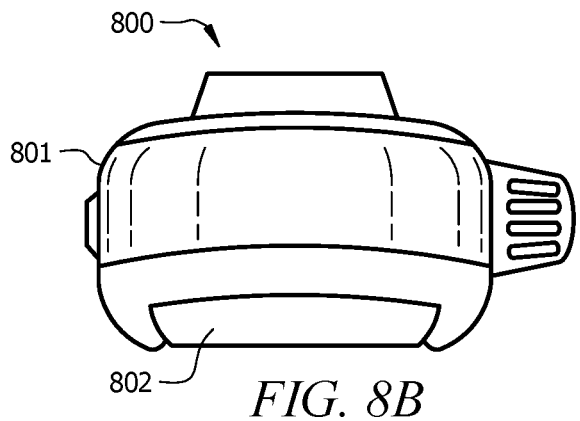
Figure 8C:
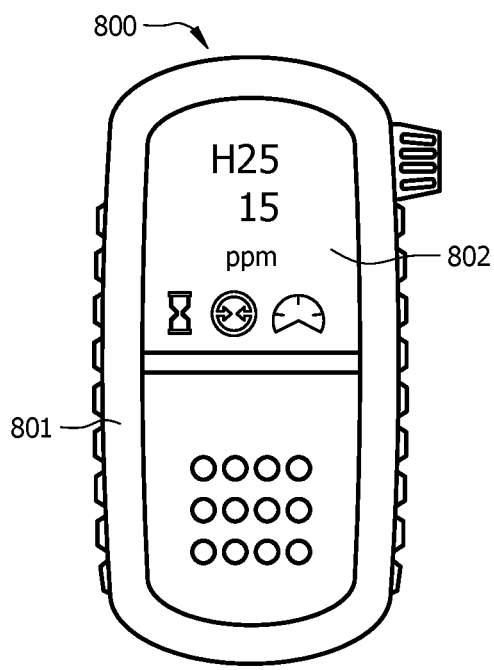
Figure 8D:
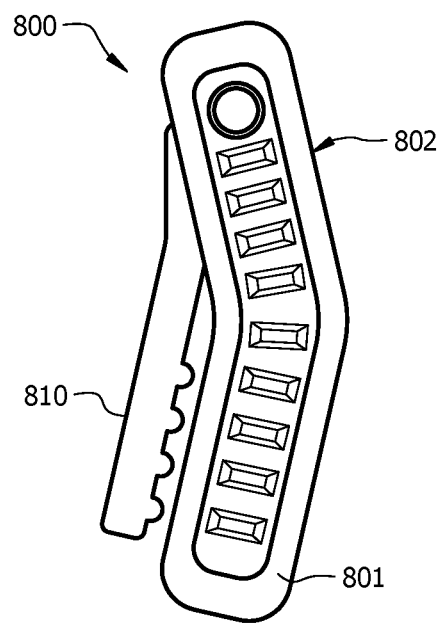

Referring to FIGS. 7A-7B, a gas detector 700 may be configured to interface with a portable calibration and maintenance dock 720. The dock 720 may be configured to communicate with the gas detector 700 via a wired or wireless system to complete calibration, bump tests and/or data logging, and the dock 720 may be connected via a wireless or wired connection to a desktop computer and/or smart device. The dock 720 may be battery powered to allow for in-field calibration and maintenance. The dock 720 may be self-contained and may not be attached to another device or container. The dock 720 may be small, low cost, portable, and battery powered. The dock 720 may comprise one or more sample gas for completing calibration and/or testing. The dock 720 may also be integrated into a carry case for the gas detector 700, providing dual functionality. Gas could be delivered via small volume containers or pods that are located within or attached to the dock 720. The small volume containers could be punctured when the device needs to be bump tested for a one time use.

Referring to FIGS. 8A-8D, a gas detector 800 may comprise an angled housing 801 and/or display 802, which may be angled towards the user when the gas detector 800 is worn by the user. The angle of the housing 801 may improve visibility of the display 802 when the gas detector 800 is attached to clothing (or otherwise worn by the user), such as via a clip 810. The angled housing 801 may also improve the fit against the user's body, particularly if the gas detector 800 is attached on the upper arm or shoulder. The gas detector 800 may comprise a housing 801 that is angled less than approximately 180° to provide an angled display that is angled toward a user's face when the gas detector 800 is worn by the user.

Figure 9A:
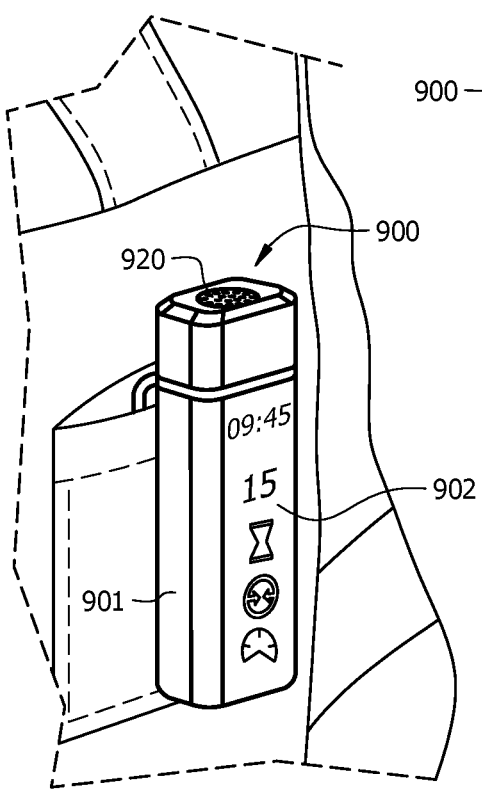
FIGS. 9A-9D illustrate a gas detector according to an embodiment of the disclosure.
Figure 9B:
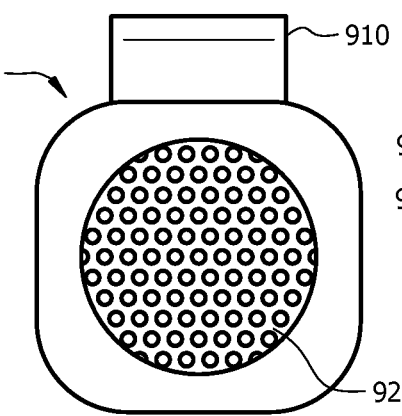
Figure 9C:
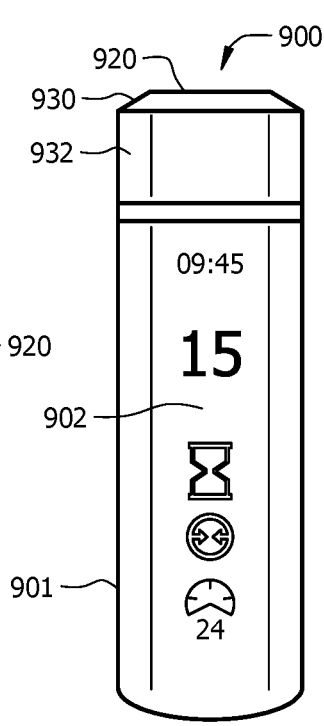
Figure 9D:
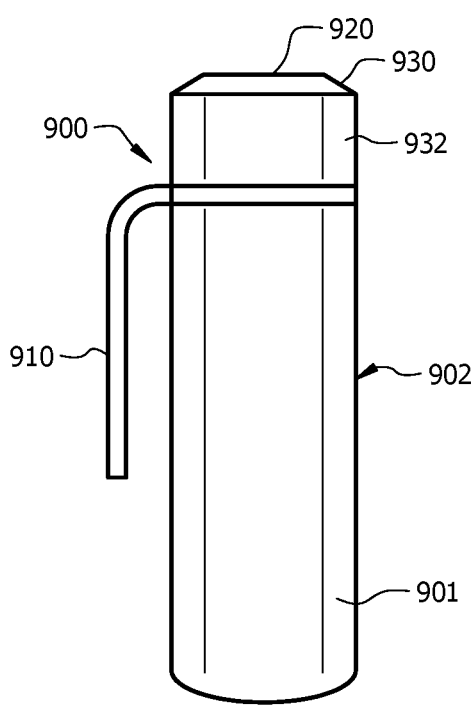
Figure 9E:
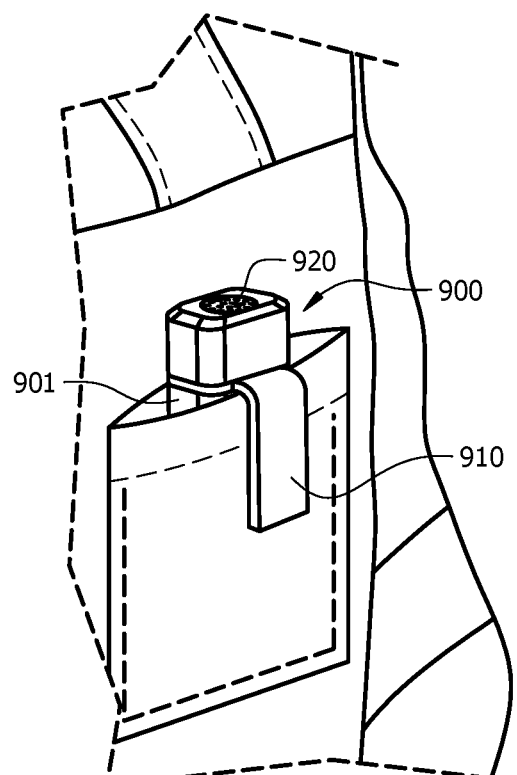
Figure 10A:
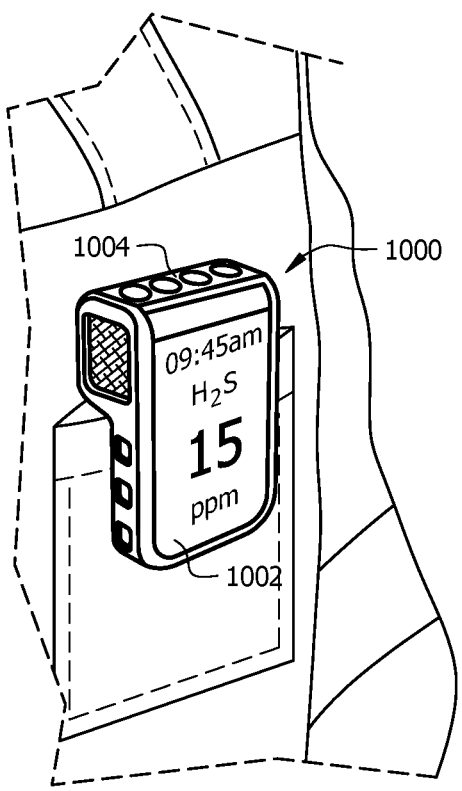
FIGS. 10A-10D illustrate a gas detector according to an embodiment of the disclosure.
Figure 10B:
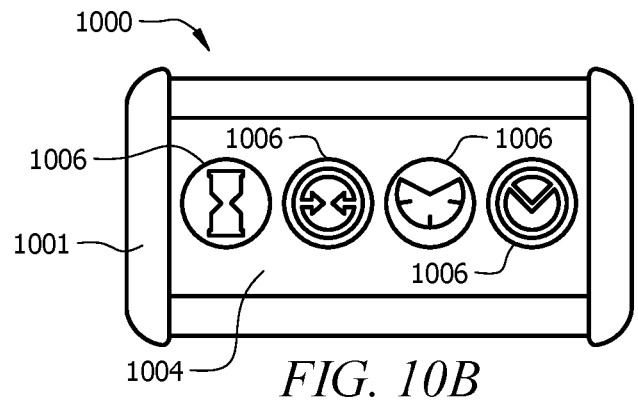
Figure 10C:
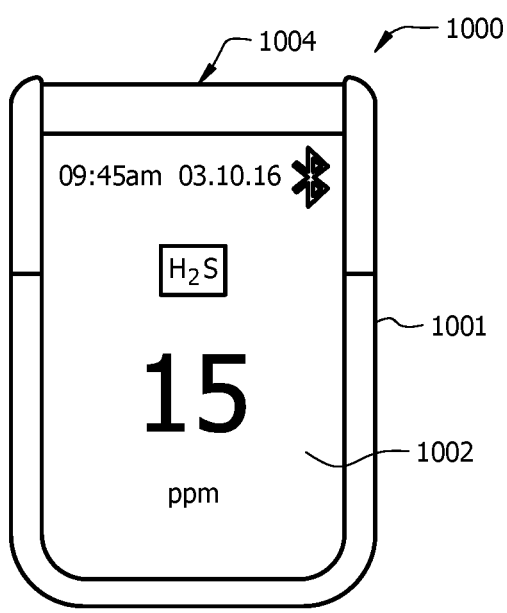
Figure 10D:
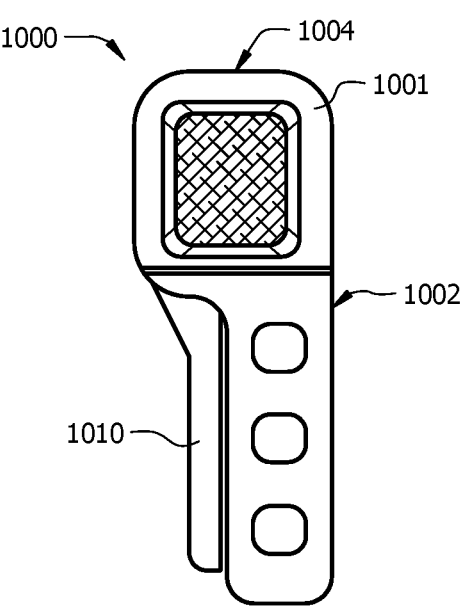

Referring to FIGS. 9A-9E, a gas detector 900 may comprise a cylindrical housing 901 with at least one sensor 920 located at the top of the housing 901. The tube-shaped, rounded housing 901 allows the gas detector 900 to be worn inside or outside a pocket, as shown in FIGS. 9A and 9E, and may prevent snagging when inserted or removed from the pocket. The sensor 920 located at the top of the housing 901 may be located above the clip 910, allowing the gas detector 900 to be worn in a pocket (held by the clip 910) while still allowing the sensor 900 to receive sample gases from the ambient environment. In some embodiments, the gas detector 900 may comprise one or more indicators 930, 932 located near the top of the housing 901, wherein the indicators 930, 932 may extend from the pocket when the gas detector 900 is worn in the pocket. For example, the indicators 930, 932 may be located above the attachment clip 910 of the gas detector. The indicators 930, 932 may comprise lights, such as LEDs, and may cover the sides of the top portion and/or the top surface. The gas detector 900 may also comprise a more detailed display 902, where the indicators 930, 932 provide only minimal, essential information, such as alarm status.

In some embodiments, a gas detector may comprise an adjustable display attached to a sensor via a hinge, which may allow for adjustment of the display at an angle with respect to the sensor portion of the gas detector. The gas detector may be worn with the display on the top or the bottom, and the hinge may allow the display to be adjusted toward the user's face. In some embodiments, on adjustment of the display via the hinge, the display may auto-rotate for easier readability by the user. For example, a sensor located within the hinge may indicate when the gas detector has been adjusted and/or the orientation of the gas detector may be sensed (e.g. with display located above or below the sensor portion of the gas detector and/or attachment clip), and optionally which angle and/or direction the hinge is set at.

Referring to FIGS. 10A-10D, a gas detector 1000 may comprise a first display 1002 and a second display 1004. The first display 1002 may comprise a larger, more detailed display, wherein the orientation of the first display 1002 may be adjustable. The second display 1004 may comprise a top surface display, and may be located on a top surface of the housing 1001 of the gas detector 1000. The top surface display 1004 may be positioned for easy viewing when the gas detector 1000 is worn by a user, such as on the user's clothing or belt. In some embodiments, the first display 1002 of the gas detector 1000 may be configured to rotate when the device moved in a certain way by the user. When attached to the user in a typical manner, with the first display 1002 front facing, the display may be oriented such that someone facing the user may be able to read the display. The clip 1010 may allow for the gas detector 1000 to be lifted up to be viewed by the user. In some embodiments, the first display 1002 (and/or gas detector 1000) may be attached to the user (via their clothing) on a hinge or pivot, such that a portion of the gas detector 1000 and/or display 1002 may be easily rotated toward the user's face. When the gas detector 1000 and/or display 1002 are rotated, the orientation of the display 1002 may automatically change so that the user may view the display 1002 in the right direction.

In some embodiments, the top surface display 1004 may comprise one or more indicators 1006 (e.g. where the top surface display 1004 may be separate from the main display 1002). Critical status information may be communicated to the user via the indicators 1006. The indicators 1006 may provide basic information at a quick glance for the user, such as a confidence signal that the detector is functioning correctly, battery power is sufficient, and the atmosphere is safe, for example. This may allow a quick reference for the user, where the user may also consult the main (first) display 1002 located on the front surface of the gas detector 1000 if more information is desired.

In some embodiments, the displays 1002 and 1004 of the gas detector 1000 may comprise a color touchscreen display and/or gestured-controlled display, with adaptive capability. In some embodiments, the first display 1002 may comprise a color display comprising substantially the entire front surface of the gas detector 1000, providing improved visibility to the user and other workers around the user. In some embodiments, the display 1002 may be configured to show more than one sensor reading. In some embodiments, the display 1002 may be configured to rotate between vertical and horizontal orientations depending on how the gas detector is attached to the user and/or oriented.

Figure 11A:
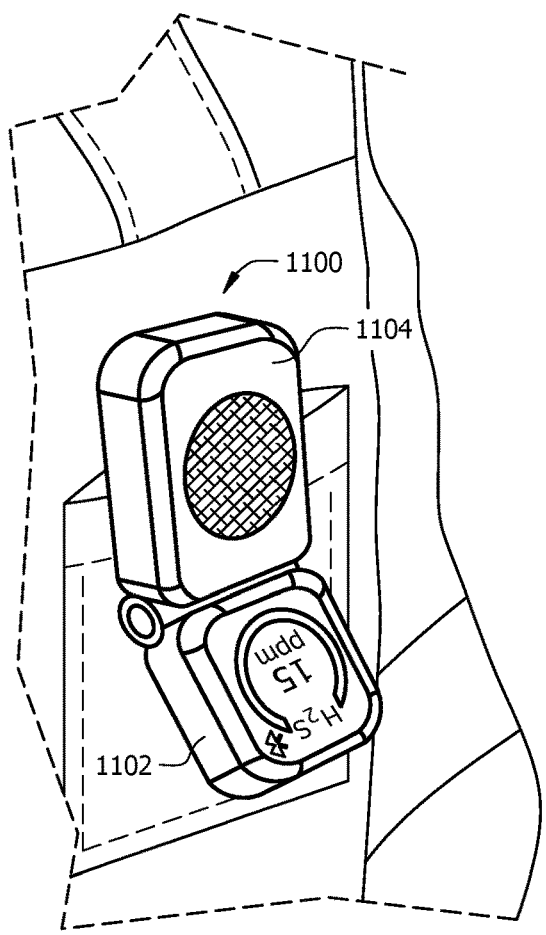
Figure 11B:
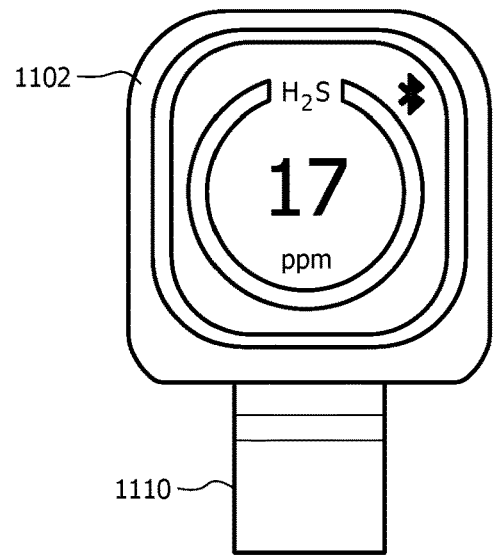
Figure 11C:
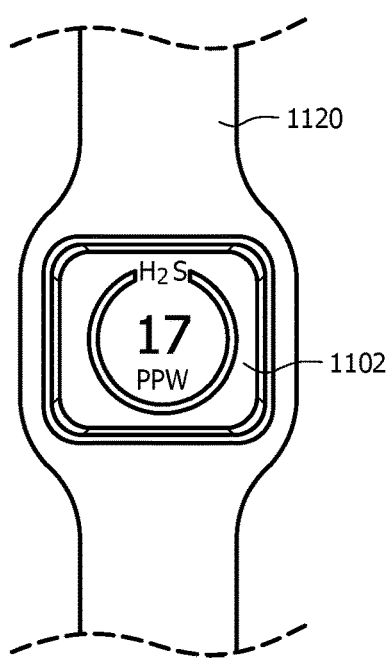

Referring to FIGS. 11A-11C a gas detector 1100 may comprise separate modules, such as a display module 1102 and a sensor module 1104, which can be connected together and worn as a single device (as shown in FIG. 11A), and/or may be separated (e.g. removably joinable). When separated, the sensor module 1104 may be worn within the breathing zone of the user (e.g. which may be within twelve inches of the user's mouth), while the display module 1102 may be positioned elsewhere for easier viewing. For example, shown in FIG. 11B, the display module 1102 may be attached to a clip 1110 enabling the display module 1102 to be clipped onto another surface. As another example, shown in FIG. 11C, the display module 1102 may be attached to a band accessory 1120 and fitted around the wrist or forearm of the user. So for example, the removable attachment mechanism (for removably joining the sensor module 1104 and the display module 1102) may also optionally allow each element to be separately attached (for example to the user's clothing and/or a wrist band). Wireless connectivity between the sensor module 1104 and display module 1102 may provide communication, and the modules may be battery powered.

Figure 12A:
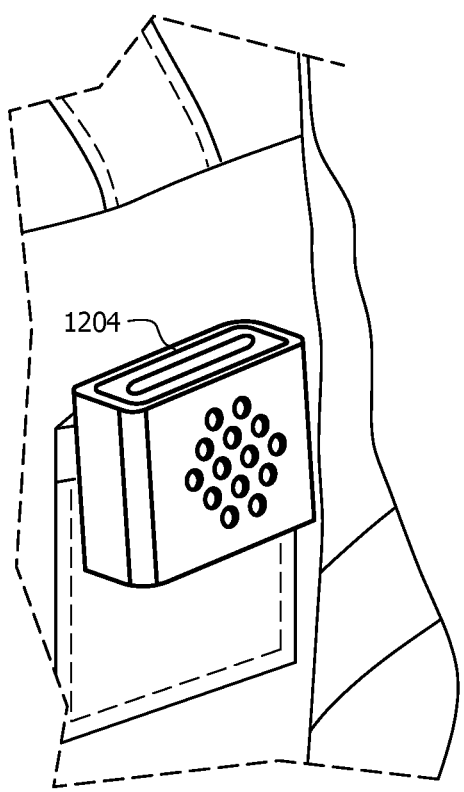
FIGS. 12A-12D illustrate a gas detector according to an embodiment of the disclosure.
Figure 12B:
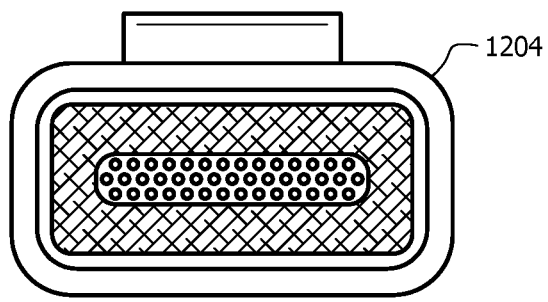
Figure 12C:
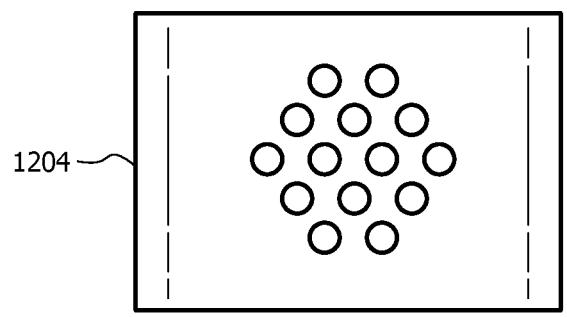
Figure 12D:
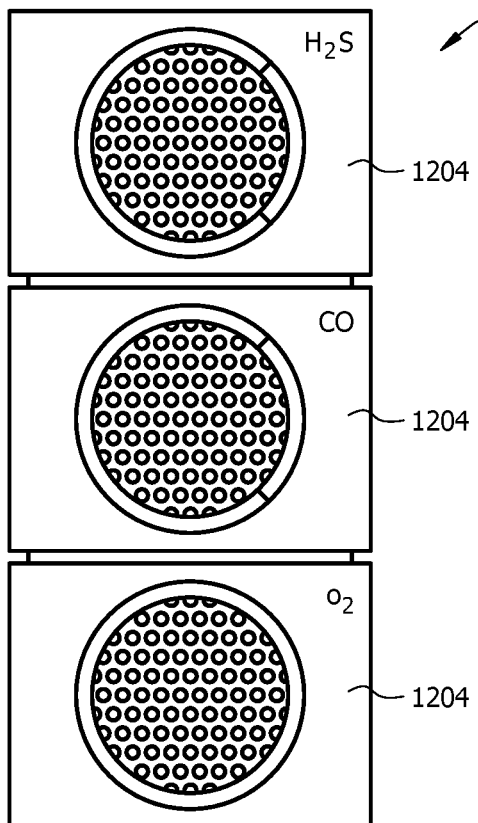
Figure 12E:
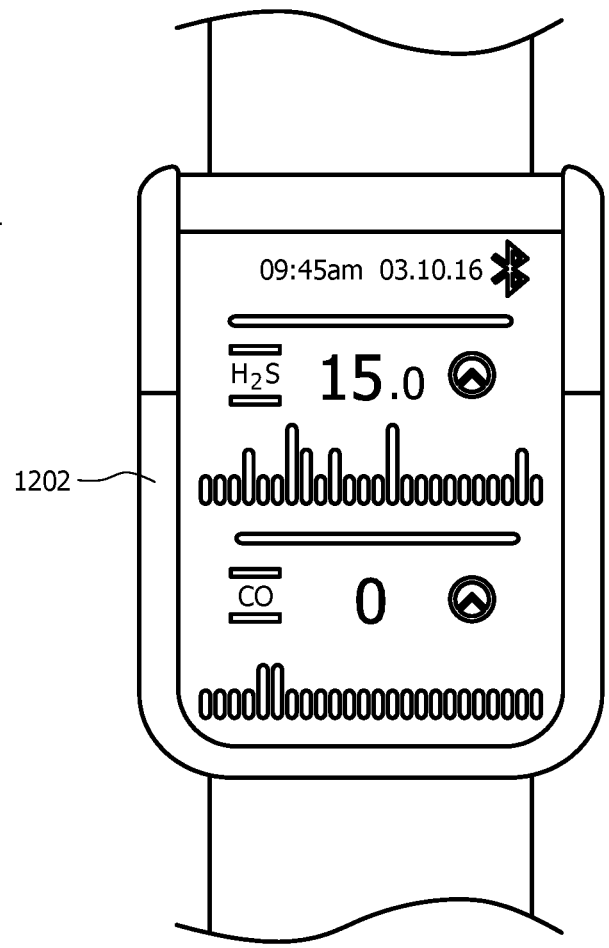

Referring to FIGS. 12A-12E, a gas detector 1200 may comprise one or more single gas sensor modules 1204 that can be physically connected or worn together to form a multi-gas sensor (e.g. configured to jointly detect any number of gases), as shown in FIG. 12D. A display 1202 may also be a separate module that can be connected to the sensor modules 1204 (e.g. may comprise an attachment mechanism which allows attachment to at least one of the sensor modules 1204). Alternatively, the sensor modules 1204 may communicate with an application on a mobile device (such as a smart phone or smart watch). The display 1202 (whether connected or wireless) may control all functions of the sensor modules 1204, such as set up, activation, and maintenance requirements. Connectivity between sensor modules 1204 could be wireless and/or physical. In some embodiments, the detector of FIGS. 12A-12E is a system of (a plurality of) separate gas detector/sensor elements/modules, all of which may be in communication (e.g. via a wireless transmitter or transceiver) with a display element (which in some embodiments may be a smart phone or other wireless device wirelessly communicating with the detector elements), which each might comprise an attachment mechanism configured to allow attachment of one detector element to another and/or to a user's clothing.

In some embodiments, a gas detector may comprise a battery powered wearable dock, which can be incorporated into a hand strap, arm band, clip or clothing. The dock is able to receive and power a variety of sensor units and communication modules such as single and multi-gas sensors, physiological tracking sensors, motion/accelerometers, and a Wi-Fi, Bluetooth and GPS communications hub for connecting worker devices. The sensor units and communication modules may comprise a uniform design, wherein the power supply connection, shape, size, and other integrations may be the same for every module or unit. In some embodiments, the dock itself may comprise wireless communication and/or power supply.

Figure 13A:
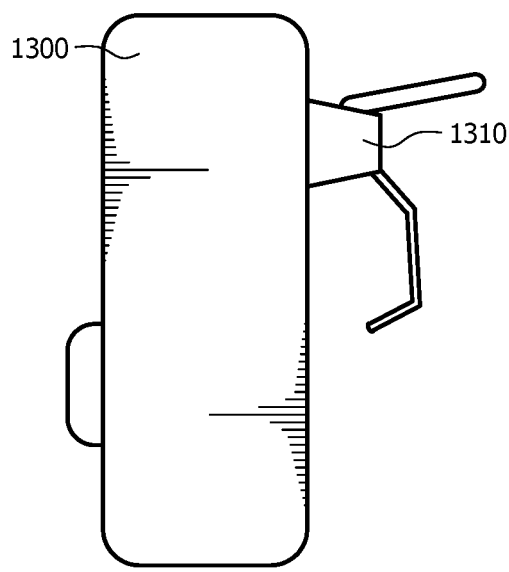
FIGS. 13A-13B illustrate an attachment sensor according to an embodiment of the disclosure.
Figure 13B:
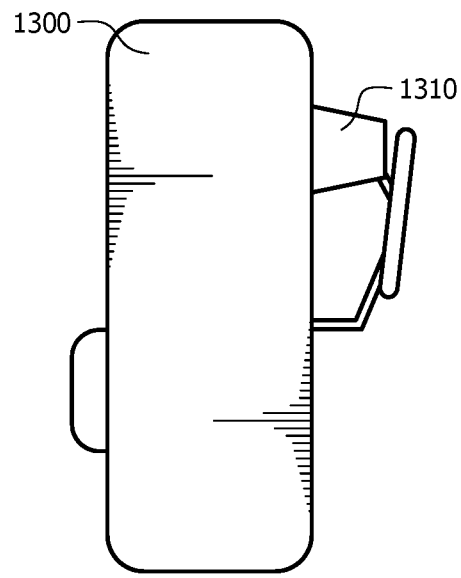

Referring to FIGS. 13A-13B, a gas detector 1300 may be configured to automatically activate and/or deactivate power and/or settings based on if the gas detector is attached to a user or not. The gas detector 1300 may sense when the gas detector is worn via the attachment clip 1310. When the clip 1310 is closed (as in FIG. 13B), the gas detector 1300 may be activated or turned on. When the clip 1310 is opened (as in FIG. 13A), the gas detector 1300 may be put into sleep mode or deactivated. Alternatively, when the clip 1310 is closed, the gas detector 1300 may be switched to a "safe worker mode" with functional options limited to 'on the job' requirements. When the clip 1310 is opened, full functions may be available to the user, such as for set up, maintenance and data logging etc.

Figure 14A:
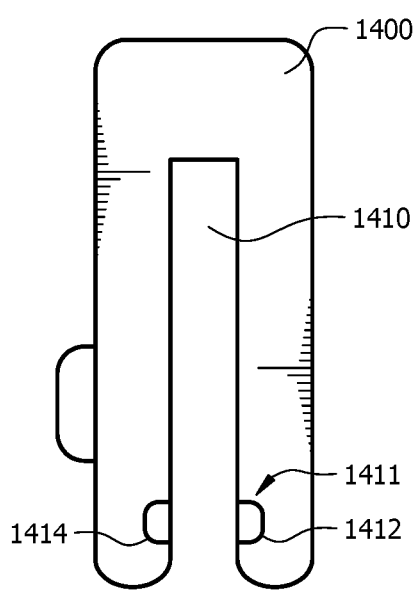
FIGS. 14A-14B illustrate an attachment sensor according to an embodiment of the disclosure.
Figure 14B:
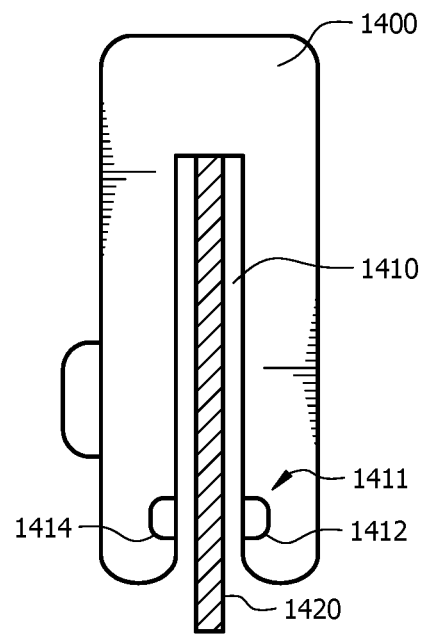

Referring to FIGS. 14A-14B, a gas detector 1400 may be configured to automatically activate and/or deactivate power and/or settings based on if the gas detector is attached to a user or not. The gas detector 1400 may sense when the gas detector 1400 is worn via a sensor 1411 within the attachment slot 1410. The sensor 1411 may comprise a light emitter 1412 and a light detector 1414. When the gas detector 1400 has been attached to a layer of fabric 1420 or other material, light is not received by the light detector 1414 (indicating the gas detector is worn as shown in FIG. 14B), and the gas detector 1400 may be activated or turned on. When light is received by the light detector 1414 (indicating the gas detector is not worn as shown in FIG. 14A), the gas detector 1400 may be put into sleep mode or deactivated. Alternatively, when light is not received by the light detector 1414, the gas detector 1400 may be switched to a "safe worker mode" with functional options limited to 'on the job' requirements. When light is received by the light detector 1414, full functions may be available to the user, such as for set up, maintenance and data logging etc.

Figure 15:
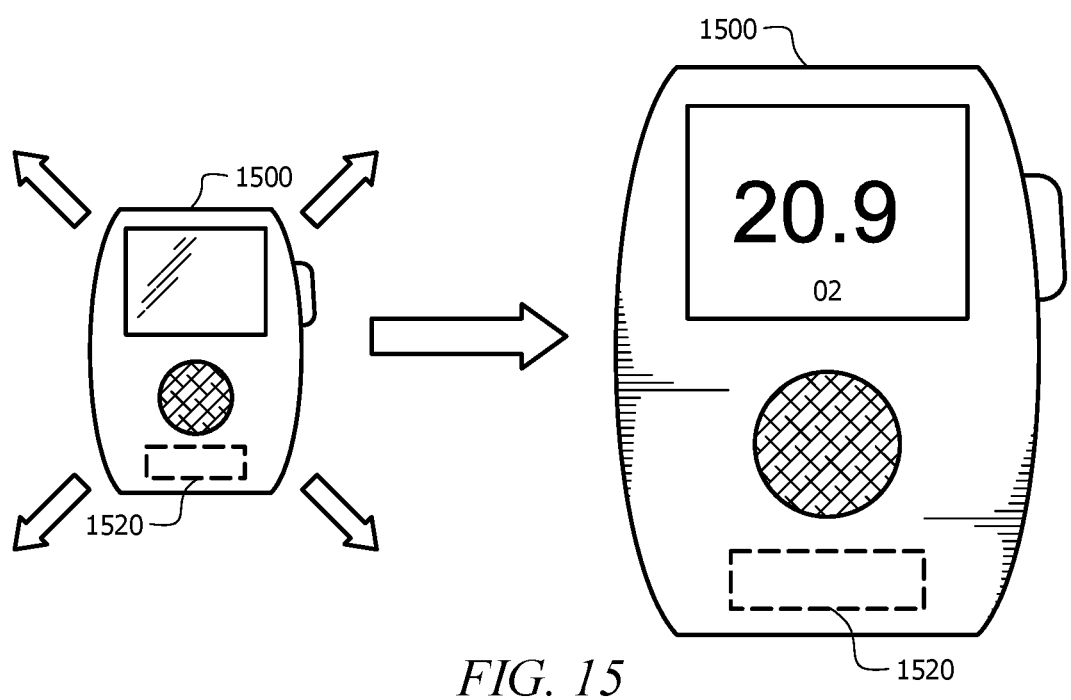
FIG. 15 illustrates a method for detecting if a gas detector is worn according to an embodiment of the disclosure.

Referring to FIG. 15, a gas detector 1500 may be configured to automatically activate and/or deactivate power and/or settings based on if the gas detector 1500 is attached to a user or not. The gas detector 1500 may sense when the gas detector is worn via a motion sensor 1520 within the gas detector 1500. When motion is detected (indicating the gas detector is worn and carried by a user), the gas detector 1500 may be activated or turned on. When motion is not detected (e.g. for a pre-set (e.g. significant) period of time, which might indicate that the gas detector is not worn), the gas detector 1500 may be put into sleep mode or deactivated. Alternatively, when motion is detected, the gas detector 1500 may be switched to a "safe worker mode" with functional options limited to 'on the job' requirements. In some embodiments, motion would not be deemed to be detected unless the level of motion met a pre-set threshold (e.g. only significant motion would be effective). When motion is not detected, full functions may be available to the user, such as for set up, maintenance and data logging etc.

Having described device and method embodiments above, especially with regard to the figures, various additional embodiments can include, but are not limited to:

Embodiments of the disclosure may comprise a communication system comprising a plurality of wireless gas detectors, wherein the plurality of gas detectors are operable to communicate with one another (including settings, updates, collected data, and alarm status); and a central monitoring station, wherein the central monitoring station is operable to simultaneously update settings on the plurality of gas detectors as needed.

Embodiments of the disclosure may comprise a gas detector module comprising at least one sensor; a display; a processor; a memory; and an interface, wherein the interface is operable to removably connect to a plurality of wearable accessories, wherein the wearable accessories comprise one or more of the following: wrist band, forearm band, upper arm band, clip, strap, and/or pendant strap.

Embodiments of the disclosure may comprise a gas detector comprising at least one gas sensor; a soft sensor pack operable to house the at least one gas sensor; and one or more attachments operable to secure the soft sensor pack to clothing worn by the user, wherein the attachment(s) comprise one or more of: zippers, stitching, pockets, loops, hook-and-loop, and/or Velcro.

Embodiments of the disclosure may comprise a gas detector comprising at least one sensor; and a large flexible display in communication with the at least one sensor, wherein the large flexible display is operable to fit over a portion of the user's body, such as the upper arm.

Embodiments of the disclosure may comprise a gas detector comprising at least one sensor; a display; and a hinge or pivot attached to the display, wherein the display can be rotated about the hinge or pivot, and wherein the display is operable to automatically switch directions when rotate about the hinge or pivot, such that the display is oriented for the user looking at the display.

Embodiments of the disclosure may comprise a gas detector comprising at least one sensor; and a light band comprising lights around the circumference of the band operable to communicate with the at least one sensor, wherein the band is operable to indicate the status of the worker via light colors and/or flashing lights, and wherein the band is worn by the user, such as on the arm or leg of the user.

Embodiments of the disclosure may comprise a gas detector comprising at least one sensor; an access lid operable to lift to allow access to the interior elements of the gas detector, wherein the sensor may be replaced by lifting the access lid; and a sensor receptacle located below the access lid, wherein the sensor is threaded or otherwise secured into the sensor receptacle.

Embodiments of the disclosure may comprise a method for preventing deactivation of a gas detector comprising one or more of the following steps: turning off the gas detector by connection with an external element, wherein the gas detector does not have an on/off switch; providing a two-step on/off switch, to prevent accidental turn off; providing an on/off switch located on the back or underside of the gas detector, making it difficult to turn off the detector and protecting from accidental turn off; providing a code-lock or other wireless lock on the gas detector, wherein the gas detector may not be turned off without the code or other key; automatically notifying a supervisor when the detector is turned off, via text messaging, email, or other wireless communication; and/or providing a gas detector that remains activated without an off state, wherein the battery is activated and remains activated until it drains or requires charging.

Embodiments of the disclosure may comprise a portable dock for calibration and maintenance of a gas detector comprising a portable housing operable to receive and hold a gas detector; a processor operable to communicate with the gas detector (wirelessly or wired) to complete calibration and testing; and a single-use gas container or pod, wherein the container supplies the gas to the gas detector for testing.

Embodiments of the disclosure may comprise a modular platform operable to be worn by a user comprising a wearable dock comprising a power supply; and a plurality of modules (or units) operable to fit onto the wearable dock, wherein the plurality of modules comprise a uniform size, shape, and configuration for power supply, and wherein the modules comprise one or more of the following: sensor modules, communication modules, gas sensors, physiological trackers, motion sensors, Wi-Fi modules, Bluetooth modules, and/or GPS modules.

In an embodiment of the disclosure, a gas detector may comprise at least one gas sensor; a display; and an attachment clip comprising a rotating ratchet configured to lock into a position unless rotated by a user, and configured to rotate the display about the attachment clip.

In an embodiment of the disclosure, a gas detector may comprise at least one gas sensor; a display; and an attachment clip comprising an attachment sensor configured to indicate if the gas detector is worn by a user. In some embodiments, at least a portion of the display is configured to rotate when the attachment sensor indicates that the gas detector is worn by a user. In some embodiments, when the attachment sensor indicates that the gas detector is worn, the device is powered on or activated. In some embodiments, when the attachment sensor indicates that the gas detector is not worn, the device is powered off or deactivated. In some embodiments, when the attachment sensor indicates that the gas detector is worn, the device is switched into a "safe worker mode" with limited functions available to the user. In some embodiments, when the attachment sensor indicates that the gas detector is not worn, the device is switch into a full function mode.

In an embodiment of the disclosure, a gas detector may comprise at least one gas sensor; a display; and a rotary dial configured to control the display, and navigate through multiple menus on the display.

In an embodiment of the disclosure, a gas detector may comprise at least one gas sensor; a display; and a housing that is angled less than approximately 180°, wherein the display is located on at least one half of the housing, and wherein the display is angled toward a user's face when the gas detector is worn by the user.

In an embodiment of the disclosure, a gas detector may comprise at least one gas sensor; a display; a housing that is cylindrical in shape, wherein the at least one gas sensor is located on the top surface of the housing (i.e. a flat end surface of the cylinder); one or more indicators located on the top portion of the housing, near the sensor; and an attachment clip located below the sensor and the one or more indicators.

In an embodiment of the disclosure, a gas detector may comprise at least one gas sensor; a display; a hinge located between the display and the at least one sensor, wherein the hinge is configured to rotate the display with respect to the at least one gas sensor, and wherein the hinge comprises a sensor configured to indicate the angle at which the hinge is rotated. In some embodiments, the display is configured to rotate when the sensor in the hinge indicates that the hinge has been rotated more or less than flat (or 180° angle). In some embodiments, the gas detector may further comprise an attachment clip attached to the at least one gas sensor.

In an embodiment of the disclosure, a gas detector may comprise a first module comprising at least one gas sensor; a second module comprising a display; and an attachment configured to removably attach the first module to the second module, wherein the first module is located within a breathing zone of a user, and wherein when the second module is removed from the first module, the second module is located within a viewing zone of the user.

In an embodiment of the disclosure, a gas detector may comprise a first module comprising a first gas sensor; a second module comprising a second gas sensor; an attachment configured to removably attach the first module to the second module; and a third module configured to wirelessly communicate with at least one of the first module and the second module, wherein the third module comprises a display. In some embodiments, the gas detector may further comprise a plurality of modules comprising a plurality of gas sensors configured to physically attach to one another. In some embodiments, the third module comprises a mobile device.

In an embodiment of the disclosure, a method for activating and deactivating power and/or settings of a gas detector may comprise one or more of the following steps: determining that the gas detector is worn by a user; activating the power of the gas detector; activating a safe worker mode with limited functionality; determining that the gas detector is not worn by a user; deactivating the power of the gas detector; and deactivating a safe worker mode with limited functionality, thereby allowing full functionality. In some embodiments, determining that the gas detector is worn by a user comprises determining that an attachment clip is closed. In some embodiments, determining that the gas detector is not worn by a user comprises determining that an attachment clip is open. In some embodiments, determining that the gas detector is worn by a user comprises determining that an attachment slot has part of the user's clothing within the slot. In some embodiments, determining that the gas detector is not worn by a user comprises determining that an attachment slot has nothing within the slot. In some embodiments, determining that the gas detector is worn by a user comprises detecting motion of the gas detector. In some embodiments, determining that the gas detector is not worn by a user comprises detecting non-motion of the gas detector.

It should be understood that any of the embodiments described above (and/or any of the elements/aspects of such embodiments) might be combined into a joint embodiment. For example, the screen rotation (e.g. auto-rotate feature, when the screen rotates the image/text depending on the orientation of the display) could be used for any described gas detector embodiment having a display (and an attachment mechanism, which might allow attachment of the gas detector to the user's clothing in a plurality of orientations).

In a first embodiment, a gas detector may comprise at least one gas sensor configured to detect at least one gas in the ambient environment; a display configured to display information received from the at least one gas sensor; an attachment configured to attach the gas detector to a user; an attachment sensor configured to detect when the gas detector has been attached to a user; and a processor configured to receive information from the attachment sensor, and configured to automatically control the orientation of the display based on information received from the attachment sensor.

A second embodiment may include the gas detector of the first embodiment, wherein at least a portion of a screen of the display is configured to rotate when the attachment sensor indicates that the gas detector is worn by a user.

A third embodiment may include the gas detector of the first or second embodiments, wherein, when the attachment sensor indicates that the gas detector is worn by a user, the gas detector is powered on or activated.

A fourth embodiment may include the gas detector of any of the first to third embodiments, wherein, when the attachment sensor indicates that the gas detector is not worn, the gas detector is powered off or deactivated.

A fifth embodiment may include the gas detector of any of the first to fourth embodiments, wherein, when the attachment sensor indicates that the gas detector is worn, the gas detector is switched into a "safe worker mode" with limited functions available to the user.

A sixth embodiment may include the gas detector of any of the first to fifth embodiments, wherein, when the attachment sensor indicates that the gas detector is not worn, the gas detector is switch into a full function mode.

A seventh embodiment may include the gas detector of any of the first to sixth embodiments, wherein, when the attachment sensor indicates that the gas detector is worn, the display is oriented toward a user wearing the gas detector and looking at the display.

A eighth embodiment may include the gas detector of any of the first to seventh embodiments, wherein, when the attachment sensor indicates that the gas detector is not worn, the display is oriented toward a user looking at the display and standing near another person who is wearing the gas detector.

A ninth embodiment may include the gas detector of any of the first to eighth embodiments, wherein the attachment comprises an attachment clip comprising a rotating ratchet configured to lock into a position unless rotated by a user, and configured to rotate the display about the attachment clip.

A tenth embodiment may include the gas detector of any of the first to ninth embodiments, wherein the attachment comprises one or more openings configured to attach the gas detector to a strap or loop.

In an eleventh embodiment, a method for controlling the orientation of the display of a gas detector may comprise indicating that the gas detector is being worn by a user; automatically changing the orientation of the display when the gas detector is worn by a user; indicating that the gas detector is not being worn by a user; and automatically changing the orientation of the display when the gas detector is not worn by a user.

A twelfth embodiment can include the method of the eleventh embodiment, wherein indicating that the gas detector is being worn by a user comprises attaching the gas detector to a user; and detecting by an attachment sensor that the gas detector is being worn by a user.

A thirteenth embodiment can include the method of the eleventh or twelfth embodiments, further comprising detecting at least one gas in the ambient environment; and displaying the detected information via the display.

A fourteenth embodiment can include the method of any of the eleventh to thirteenth embodiments, further comprising indicating that the gas detector is worn by a user; activating the power of the gas detector; indicating that the gas detector is not worn by a user; and deactivating the power of the gas detector.

A fifteenth embodiment can include the method of any of the eleventh to fourteenth embodiments, further comprising indicating that the gas detector is worn by a user; activating a safe worker mode with limited functionality; indicating that the gas detector is not worn by a user; and deactivating a safe worker mode with limited functionality, thereby allowing full functionality.

In a sixteenth embodiment, a gas detector may comprise at least one gas sensor configured to detect at least one gas in the ambient environment; a display configured to display information received from the at least one gas sensor; and a hinge or pivot attached to the display, wherein the display can be rotated about the hinge or pivot, and wherein the display is operable to automatically switch orientation when rotated about the hinge or pivot, such that the display is oriented toward a user looking at the display.

A seventeenth embodiment may include the gas detector of the sixteenth embodiment, wherein the display is oriented toward a user wearing the gas detector and looking at the display.

A eighteenth embodiment may include the gas detector of the sixteenth or seventeenth embodiments, wherein the display is oriented toward a user looking at the display and standing near another person who is wearing the gas detector.

A nineteenth embodiment may include the gas detector of any of the sixteenth to eighteenth embodiments, wherein the hinge is configured to rotate in a first direction allowing the user wearing the gas detector to lift the display out away from the user's body.

A twentieth embodiment may include the gas detector of any of the sixteenth to nineteenth embodiments, wherein the hinge is configured to rotate in a second direction allowing the user wearing the gas detector to rotate the display adjacent to the user's body.

A twenty-first embodiment may include the gas detector of any of the sixteenth to twentieth embodiments, further comprising a sensor configured to detect when the display has been rotated about the hinge or pivot, and a processor configured to automatically control the orientation of the display based on information received from the sensor.

A twenty-second embodiment may include the gas detector of any of the sixteenth to twenty-first embodiments, further comprising a second display located on a top surface of the gas detector, wherein the second display comprises simple icons, and wherein the second display is separate from the first, main display.

A twenty-third embodiment may include the gas detector of any of the sixteenth to twenty-second embodiments, wherein the hinge or pivot comprises an attachment clip comprising a rotating ratchet configured to lock into a position unless rotated by a user, and configured to rotate the display about the attachment clip.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector comprising:
   at least one gas sensor configured to detect at least one gas in an ambient environment;
   a display configured to display information received from the at least one gas sensor;
   an attachment configured to attach the gas detector to a user;
   an attachment sensor configured to detect when the gas detector has been attached to the user; and
   a processor configured to receive information from the attachment sensor, and configured to automatically control orientation of at least a portion of the display based on the information received from the attachment sensor which indicates that the gas detector is worn by the user.

2. The gas detector of claim 1, wherein, when the attachment sensor indicates that the gas detector is worn by the user, the gas detector is powered on or activated.

3. The gas detector of claim 1, wherein, when the attachment sensor indicates that the gas detector is not worn, the gas detector is powered off or deactivated.

4. The gas detector of claim 1, wherein, when the attachment sensor indicates that the gas detector is worn, the gas detector is switched into a "safe worker mode" with limited functions available to the user.

5. The gas detector of claim 1, wherein, when the attachment sensor indicates that the gas detector is not worn, the gas detector is switched into a full function mode.

6. The gas detector of claim 1, wherein, when the attachment sensor indicates that the gas detector is worn, the display is oriented toward the user wearing the gas detector and looking at the display.

7. The gas detector of claim 1, wherein, when the attachment sensor indicates that the gas detector is not worn, the display is oriented toward a user looking at the display.

8. The gas detector of claim 1, wherein the attachment comprises an attachment clip comprising a rotating ratchet configured to lock into a position unless rotated by the user, and configured to rotate the display about the attachment clip.

9. The gas detector of claim 1, wherein the attachment comprises one or more openings configured to attach the gas detector to a strap or loop.

10. A method for controlling orientation of a display of a gas detector, the method comprising:
indicating, by an attachment sensor, that the gas detector is being worn by a user;
receiving, by a processor, information from the attachment sensor indicating that the gas detector is being worn by the user; and
automatically controlling the orientation of at least a portion of the display based on the information received from the attachment sensor which indicates that the gas detector is worn by the user.

11. The method of claim 10, wherein indicating that the gas detector is being worn by the user comprises attaching the gas detector to the user; and detecting by the attachment sensor that the gas detector is being worn by the user.

12. The method of claim 10, further comprising detecting at least one gas in an ambient environment; and displaying the detected at least one gas via the display.

13. The method of claim 10, further comprising:
indicating that the gas detector is worn by the user;
activating power of the gas detector;
indicating that the gas detector is not worn by the user; and
deactivating the power of the gas detector.

14. The method of claim 10, further comprising:
indicating that the gas detector is worn by the user;
activating a safe worker mode with limited functionality;
indicating that the gas detector is not worn by the user; and
deactivating the safe worker mode with the limited functionality, thereby allowing full functionality.

15. A gas detector comprising:
at least one gas sensor configured to detect at least one gas in an ambient environment;
a display configured to display information received from the at least one gas sensor;
a hinge or pivot attached to the display, wherein the display is rotatable about the hinge or pivot, and wherein the display is operable to automatically switch orientation when rotated about the hinge or pivot, such that the display is oriented toward a user looking at the display;
a sensor configured to detect when the display has been rotated about the hinge or pivot; and
a processor configured to automatically control orientation of at least a portion of the display based on information received from the sensor which indicates that the display has been rotated about the hinge or pivot.

16. The gas detector of claim 15, wherein the hinge or pivot is configured to rotate in a first direction allowing the user wearing the gas detector to lift the display out away from the user's body.

17. The gas detector of claim 15, wherein the hinge or pivot is configured to rotate in a second direction allowing the user wearing the gas detector to rotate the display adjacent to the user's body.

18. The gas detector of claim 15, further comprising a second display located on a top surface of the gas detector, wherein the second display comprises simple icons, and wherein the second display is separate from a first display which is a main display.

19. The gas detector of claim 15, wherein the hinge or pivot comprises an attachment clip comprising a rotating ratchet configured to lock into a position unless rotated by the user, and configured to rotate the display about the attachment clip.

* * * * *